(12) United States Patent
Nathan et al.

(10) Patent No.: US 8,951,992 B2
(45) Date of Patent: Feb. 10, 2015

(54) *MYCOBACTERIUM* MEMBRANE PROTEASE AS A TARGET FOR INHIBITORS OF INTRABACTERIAL pH HOMEOSTASIS

(75) Inventors: Carl Nathan, Larchmont, NY (US); Sabine Ehrt, New York, NY (US); Omar Vandal, New York, NY (US); Crystal Darby, New York, NY (US)

(73) Assignee: Cornell University, Ithaca, NY (US)

( * ) Notice: Subject to any disclaimer, the term of this patent is extended or adjusted under 35 U.S.C. 154(b) by 420 days.

(21) Appl. No.: 13/000,788

(22) PCT Filed: Jul. 20, 2009

(86) PCT No.: PCT/US2009/051099
§ 371 (c)(1),
(2), (4) Date: Apr. 18, 2011

(87) PCT Pub. No.: WO2010/009456
PCT Pub. Date: Jan. 21, 2010

(65) Prior Publication Data
US 2011/0190234 A1  Aug. 4, 2011

Related U.S. Application Data

(60) Provisional application No. 61/081,944, filed on Jul. 18, 2008.

(51) Int. Cl.
| | |
|---|---|
| A61K 31/365 | (2006.01) |
| A61K 31/351 | (2006.01) |
| A61K 31/381 | (2006.01) |
| A01N 25/06 | (2006.01) |
| A01N 43/08 | (2006.01) |
| A01N 43/16 | (2006.01) |
| C12N 9/88 | (2006.01) |
| C12N 1/36 | (2006.01) |
| C12N 9/99 | (2006.01) |
| C12Q 1/18 | (2006.01) |
| G01N 33/84 | (2006.01) |

(52) U.S. Cl.
CPC .. *C12N 9/88* (2013.01); *C12N 1/36* (2013.01); *C12N 9/99* (2013.01); *C12Q 1/18* (2013.01); *G01N 33/84* (2013.01); *G01N 2333/35* (2013.01)

USPC ............ 514/61; 514/435; 514/558; 514/680; 514/685; 435/29

(58) Field of Classification Search
USPC ............... 514/61, 438, 558, 680, 685; 435/29
See application file for complete search history.

(56) References Cited

U.S. PATENT DOCUMENTS

| | | | |
|---|---|---|---|
| 5,376,682 A | | 12/1994 | Naiki et al. |
| 7,282,491 B2 * | | 10/2007 | Darwin et al. ................. 514/64 |
| 8,338,465 B2 * | | 12/2012 | Singh et al. ................... 514/369 |
| 2002/0086295 A1 * | | 7/2002 | Raz et al. ........................ 435/6 |

FOREIGN PATENT DOCUMENTS

WO    WO02/47681 A1 * 6/2002 ........... A61K 31/365

OTHER PUBLICATIONS

Merck Manual, 1992, pp. 86-89, 131 and 139-140.*
Zhang et al, Journal of Antimicrobial Chemotherapy, 2003, 52, 56-60.*
Yamaki et al, Phytotherapy Research, 1994, 8, 112-114.*
Zhang et al. "Susceptibility of *Mycobacterium tuberculosis* to Weak Acids," Journal of Antimicrobial Chemotherapy 52:56-60 (2003).
Benneche et al. "Synthesis of (E)- and (Z)-5-(Bromomethylene)furan-2(5H)-one by Bromodecarboxylation of (E)-2-(5-Oxofuran-2(5H)-ylidene)acetic Acid," Synthetic Communications 36:1401-1404 (2006).
Olsen et al. "Noninvasive Measurement of Bacterial Intracellular pH on a Single-Cell Level with Green Fluorescent Protein and Fluorescence Ratio Imaging Microscopy," Applied and Environmental Microbiology 68(8):4145-4147 (2002).
PCT International Search Report and Written Opinion for PCT/US2009/051099, mailed Oct. 21, 2009.

* cited by examiner

*Primary Examiner* — Ganapathy Krishnan
(74) *Attorney, Agent, or Firm* — LeClairRyan, a Professional Corporation

(57) ABSTRACT

The present invention is directed to methods and compounds for inhibiting bacterial growth and treating a bacterial infection in a subject. These methods involve providing an inhibitor of intrabacterial pH homeostasis, including inhibitors of the *Mycobacterium tuberculosis* Rv3671c gene encoded membrane protease. Methods for identifying novel compounds that disrupt intrabacterial pH homeostasis and their use for inhibiting bacterial growth and treating a bacterial infection in a subject are also disclosed.

11 Claims, 15 Drawing Sheets

```
Rv3671c      1  ---------------------GTGF------VISPDR--YMTNAH-------VVA-----
trypsin-2    1  IVGGYICEENSVPYQVSL----NSGYHFCGGSLISEQW--VVSAGHCYKSRIQVRL-----
elastase     1  IVGGRRARPHAWPFMVSLQLRGGHFCGAT--LIAPNF--VMSAAH-------CVANVNVR
degP/HtrA    1  ---------------------GSGV------IDADKGYVVTNNH-------VVD-----

Rv3671c     20  -------GSNNVT--------VYAGD-KPF-EATVVSYDP------SV----DVAILAV-----
trypsin-2   51  -------GEHNIE--------VLEGN-EQFINAAKIIRHPKYNSRTL---DMDILLI-----
elastase    50  AVRVVLGAHNLSRREPTRQFAVQ-RIF-EN---GYDP------VNLLNDIVILQLNGSAT
degP/HtrA   22  ------NATVIK--------VQLSDGRKF-DAKMVGKDF-----RS---DIALIQI-----

Rv3671c     52  --PHLPPPPLV---------FAAEPA------KTGADVVVLGYPGGNFTATPARIREAIRL
trypsin-2   89  --K-LSSPAVINSRVSAISLPTAPP-----AAGTESLISGW---GNTLSSGADYPDELQC
elastase   100  INANVQVAQLP----------AQGRRL------GNGVQCLAMGWGLLGRNRGI-ISVLQELNV
degP/HtrA   55  --QN---PKNL---------TAIKMADSDALRVGDYTVAIGNPFGLGETVT-SGIVSALGR Rv3671c     97  SGPDIYGD--------PEPVTRDVYTIR-----IDVEQGDGGGPLIDLNGQVLIV------
trypsin-2  138  LDAPVLSQAECEASYPGKITNNMFCVGFLEGGKDSCQGDSGGPVVS-HGELQGIVSWGYG
elastase   146  TVVTSLCR--------RSNVCTLVRGRQ------GVCFGDSGSPLV-CNGLIHGIASFVRG
degP/HtrA  101  SGLNAENY--------ENFIQTD---------GAINRGNSGALVNLNGELIGINTAILA
```

Figure 6

| strain | Erythr | Rifampin | Chloramp | Etham | INH | Strep |
|---|---|---|---|---|---|---|
| H37Rv | 1280 | 0.0120 | 8 | 1.2 | 0.05 | 1.0 |
| Rv3671c | 160 | 0.0015 | 8 | 0.6 | 0.05 | 0.25 |
| lysX | 640 | 0.0030 | 8 | 0.6 | 0.05 | 0.5 |
| erp | 40 | 0.0015 | 4 | 1.2 | 0.05 | 0.5 |

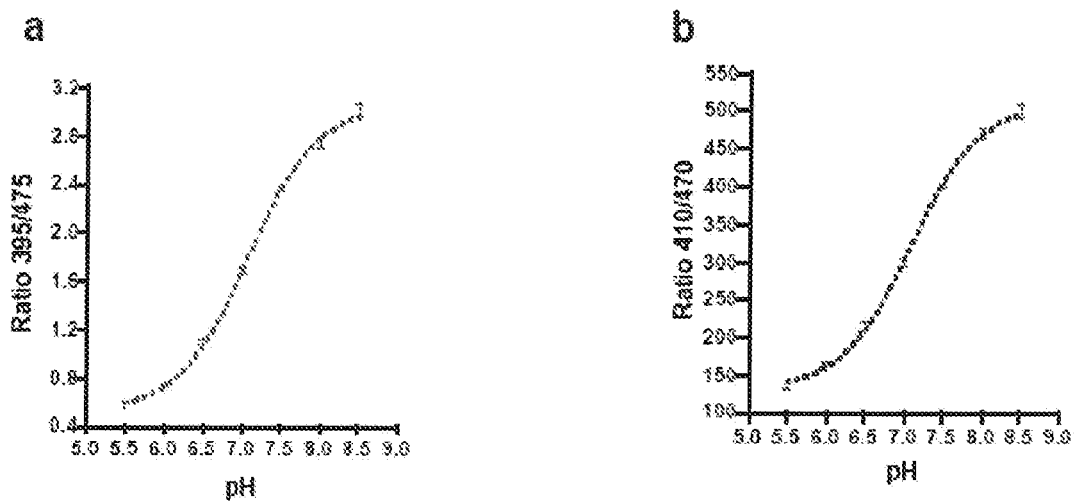
Figures 13A–B

| | Rv Number | Gene | Number of times isolated | Transposon Insertion site (nucleotide) | Name/Description | Function^ | Sensitive in 7H9-Ty-4.5+ | Sensitive in pcit-Ty-4.5# |
|---|---|---|---|---|---|---|---|---|
| 1 | Rv0007 | Rv0007 | 1 | 110 | Possible Conserved Membrane Protein | A | No | No |
| 2 | Rv0016c | pbpA | 1 | 1096 | Probable Penicillin Binding Protein | A | No | No |
| 3 | Rv0805 | Rv0805 | 1 | 6 | Unknown, Conserved Hypothetical Protein | B | No | X** |
| 4 | Rv0955 | Rv0955 | 2 | 701, 1106 | Probable Integral Membrane Protein | A | No | No |
| 5 | Rv1272c | Rv1272c | 2 | 812, 1567 | Probable ABC Transporter | A | No | X |
| 6 | Rv1273c | RV1273c | 2 | 164, 838 | Probable ABC Transporter | A | No | X |
| 7 | Rv1640c | lysX | 4 | 462, 1027, 2815, 3286 | Possible lysyl-tRNA synthetase 2 | C | Yes | No |
| 8 | Rv1781c | MalQ | 1 | 1492 | Probable 4-alpha-glucanotransferase | D | No | X |
| 9 | Rv2051c | ppm1 | 3 | 641, 1349 | Polyprenol-monophosphomannose synthase | A | No | X |
| 10 | Rv2052c | Rv2052c | 1 | 1442 | Unknown, Conserved Hypothetical Protein | A | No | X |
| 11 | Rv2115c | mpa | 1 | 1822 | Probable ATPase | A | No | No |
| 12 | Rv2136c | Rv2136c | 1 | 751 | Probable Transmembrane Protein | A | Yes | Yes |
| 13 | RV2206 | Rv2206 | 1 | 394 | Probable Transmembrane Protein | A | No | X |
| 14 | Rv2222c | glnA2 | 1 | 1341 | Glutamine Synthetase | D | No | X |
| 15 | Rv2224c | Rv2224c | 1 | 670 | Probable Exported Protease | A | Yes | No |
| 16 | Rv2379c | mbtF | 1 | 921 | Peptide Synthetase | E | No | X |
| 17 | Rv3417c | GroEL1 | 1 | 601 | Chaperonin | F | No | X |
| 18 | Rv3671c | Rv3671c | 1 | 48 | Possible Membrane Serine Protease | A | Yes | Yes |
| 19 | Rv3679 | Rv3679 | 1 | 27 | Anion Transporting ATPase | A | No | No |
| 20 | RV3680 | RV3680 | 1 | 715 | Anion Transporting ATPase | A | No | X |
| 21 | Rv3682 | ponA2 | 6 | -5, 306, 1021, 1133, 1351, 1915 | Probable Membrane Penicillin Binding Protein | A | Yes | No |

^ A cell wall and cell processes
B conserved hypothetical
C information pathways
D intermediary metabolism and respiration
E lipid metabolism
F virulence, detoxification, adaption

MYCOBACTERIUM MEMBRANE PROTEASE AS A TARGET FOR INHIBITORS OF INTRABACTERIAL pH HOMEOSTASIS

This application is a national stage application under 35 U.S.C. §371 of PCT/US2009/051099, filed Jul. 20, 2009, and claims the priority benefit of U.S. Provisional Patent Application Ser. No. 61/081,944, filed Jul. 18, 2008, which is hereby incorporated by reference in its entirety.

This invention was made with government support under grant number PO1AI056293 awarded by the National Institutes of Health. The government has certain rights in this invention.

FIELD OF THE INVENTION

The present invention is directed to methods and compounds for inhibiting bacterial growth and treating a bacterial infection in a subject.

BACKGROUND OF THE INVENTION

When Metchnikoff discovered phagocytosis, he speculated that macrophages kill most ingested microbes by acidifying them and that *Mycobacterium tuberculosis* ("Mtb") uses its waxy cell wall to resist this acidification (Metchnikoff, "Immunity to Infective Disease," Cambridge University Press; Cambridge, London, N.Y. (1905)). Subsequent studies established that after macrophages ingest particles or microbes, phagosomes with an initial pH of ~6.2 fuse with lysosomes, and their pH falls to ~4.5 (Huynh et al., "Regulation of Vacuolar pH and its Modulation by Some Microbial Species," *Microbiol Mol Biol Rev* 71:452-462 (2007) and Ohkuma et al., "Fluorescence Probe Measurement of the Intralysosomal pH in Living Cells and the Perturbation of pH by Various Agents," *Proc Natl Acad Sci USA* 75:3327-3331 (1978)). Mtb blocks phagolysosomal fusion (Armstrong et al., "Response of Cultured Macrophages to *Mycobacterium Tuberculosis*, with Observations on Fusion of Lysosomes with Phagosomes,"*J Exp Med* 134:713-740 (1971); Sturgill-Koszycki et al., "Lack of Acidification in *Mycobacterium* Phagosomes Produced by Exclusion of the Vesicular Proton-ATPase," *Science* 263:678-681 (1994); and Clemens et al., "Characterization of the *Mycobacterium Tuberculosis* Phagosome and Evidence that Phagosomal Maturation is Inhibited,"*J Exp Med* 181:257-270 (1995)); however, activation of macrophages by the T cell-derived cytokine IFN-γ overcomes the block via induction of the GTPase Lrg-47, and thus the mycobacterium-containing phagosomes acidify (MacMicking et al., "Immune Control of Tuberculosis by IFN-γ-Inducible LRG-47,*" Science* 302:654-659 (2003); Schaible et al., "Cytokine Activation Leads to Acidification and Increases Maturation of *Mycobacterium Avium*-Containing Phagosomes in Murine Macrophages," *J Immunol* 160:1290-1296 (1998); Via et al., "Effects of Cytokines on Mycobacterial Phagosome Maturation," *J Cell Sci* 111:897-905 (1998); and Sibley et al., "Intracellular Fate of *Mycobacterium Leprae* in Normal and Activated Mouse Macrophages," *Infect Immun* 55:680-685 (1987). Additionally, IFN-γ activation enhances the antimicrobial capacity of macrophages (Nathan et al., "Identification of Interferon-γ as the Lymphokine that Activates Human Macrophage Oxidative Metabolism and Antimicrobial Activity," *J Exp Med* 158:670-689 (1983)) and is essential for control of mycobacterial infection in mice and people (Nathan et al., "Local and Systemic Effects of Intradermal Recombinant Interferon-γ in Patients with Lepromatous Leprosy," *N Engl J Med;* 315:6-15 (1986); Cooper et al., "Disseminated *Tuberculosis* in Interferon-γ Gene-Disrupted Mice," *J Exp Med* 178:2243-2247 (1993); Flynn et al., "An Essential Role for Interferon-γ in Resistance to *Mycobacterium Tuberculosis* Infection," *J Exp Med* 178:2249-2254 (1993); and Dorman et al., "Clinical Features of Dominant and Recessive Interferon-γ Receptor 1 Deficiencies," *Lancet* 364:2113-2121 (2004)). Thus, acidification of the phagosome may represent a major antimycobacterial mechanism. However, IFN-γ induces hundreds of genes in macrophages (Ehrt et al., "Reprogramming of the Macrophage Transcriptome in Response to Interferon-γ and *Mycobacterium Tuberculosis*: Signaling Roles of Nitric Oxide Synthase-2 and Phagocyte Oxidase," *J Exp Med* 194:1123-1140 (2001)), among them other pathways with antimycobacterial activity, such as inducible nitric oxide synthase (Xie et al., "Cloning and Characterization of Inducible Nitric Oxide Synthase from Mouse Macrophages," *Science* 256:225-228 (1992) and MacMicking et al., "Identification of Nitric Oxide Synthase as a Protective Locus Against *Tuberculosis,"* Proc Natl Acad Sci USA* 94:5243-5248 (1997)). Because Mtb is killed to an extent, but not eradicated, in acidic phagosomes, it is unclear whether Mtb should be regarded as acid sensitive or acid resistant (Armstrong et al., "Phagosome-Lysosome Interactions in Cultured Macrophages Infected with Virulent Tubercle Bacilli. Reversal of the Usual Nonfusion Pattern and Observations on Bacterial Survival," *J Exp Med* 142:1-16 (1975); MacGurn et al., "A Genetic Screen for *Mycobacterium Tuberculosis* Mutants Defective for Phagosome Maturation Arrest Identifies Components of the ESX-1 Secretion System," *Infect Immun* 75:2668-2678 (2007)). In addition, mutants of Mtb and *Mycobacterium bovis* BCG that fail to prevent phagosome acidification are not necessarily compromised for survival in macrophages, suggesting that the bacterium can resist acid (MacGurn et al., "A Genetic Screen for *Mycobacterium Tuberculosis* Mutants Defective for Phagosome Maturation Arrest Identifies Components of the ESX-1 Secretion System," *Infect Immun* 75:2668-2678 (2007); Pethe et al., "Isolation of *Mycobacterium Tuberculosis* Mutants Defective in the Arrest of Phagosome Maturation," *Proc Natl Acad Sci USA* 101:13642-13647 (2004); and Stewart et al., "Mycobacterial Mutants with Defective Control of Phagosomal Acidification," *PLoS Pathog* 1:269-278 (2005)).

There is a continuing need to develop new anti-tuberculosis agents, especially those having unique modes of action, to ensure the availability of effective treatments against multi- and extreme-drug resistant strains. Therefore, a better understanding of *M. tuberculosis* acid resistance or sensitivity and its role in virulence is necessary. Such information will aid the development of new antibiotic agents that will complement conventional anti-tuberculosis chemotherapeutic regimens. The present invention is directed to overcoming these and other deficiencies in the art.

SUMMARY OF THE INVENTION

A first aspect of the present invention is directed to a method of inhibiting the growth of bacteria. This method involves exposing the bacteria to an agent that disrupts intrabacterial pH homeostasis under conditions effective to inhibit growth of the bacteria.

A second aspect of the present invention is directed to a method of treating a bacterial infection in a subject. This method involves administering to the subject an agent that disrupts intrabacterial pH homeostasis under conditions effective to treat the bacterial infection.

Another aspect of the present invention is directed to a method of identifying compounds that interfere with intracellular pH homeostasis of a pathogen. This method involves providing one or more candidate compounds and providing a pathogen, where the pathogen has a detectable indicator of intracellular pH. The method further involves contacting the one or more candidate compounds with the pathogen and detecting the intracellular pH of the pathogen. Detection of a change in the intracellular pH in the presence of a candidate compound identifies a compound that interferes with the intracellular pH homeostasis of the pathogen.

A number of infectious agents, particularly bacteria, have developed mechanisms to protect against environmental stresses and host-mediated defenses. Applicants have discovered that *Mycobacterium tuberculosis* (Mtb), the causative agent of tuberculosis, has developed a resistance to phagolysosomal concentrations of acid it encounters following ingestion by host macrophages, thereby facilitating the establishment of infection. The Examples presented herein demonstrate that Rv3671c, a previously uncharacterized gene encoding a membrane-associated protein, confers acid resistance and provides Mtb a mechanism to maintain its intrabacterial pH in the acidic conditions imposed by the host immune system. Rv3671c mediated acid resistance is essential for Mtb virulence, and disruption of this resistance and intrabacterial pH maintenance systems is an attractive target for chemotherapy. A number of suitable inhibitors of intrabacterial pH homeostasis are identified herein.

BRIEF DESCRIPTION OF THE DRAWINGS

FIG. 1A is a graph plotting the number of colony-forming units (CFU) of wild-type Mtb (H37Rv) at pH 4.5 or pH 6.6 in 7H9-Tw medium over the course of 15-days. The horizontal dotted line indicates the limit of detection. FIG. 1B shows the impact of medium on survival of Mtb. Mtb were plated after 6 days incubation in 7H9-Tw-4.5, 7H9-Ty-4.5, or pcit-Ty-4.5 medium, and CFU were quantified. In FIG. 1C, wild-type Mtb and five acid-sensitive mutants were plated after 6 days incubation in 7H9-Tw-4.5 or 7H9-Ty-4.5 medium, and CFU were quantified. LysX is predicted to encode a lysyl-tRNA synthetase, Rv2224c a secreted protease, and ponA2 a transglycosylase/transpeptidase. FIG. 1D is a graph showing CFU for wild-type Mtb and five acid-sensitive mutants that were plated after 6 days incubation in pcit-Ty-4.5 medium. The pH of all test media remained at pH 4.5 throughout the experiment. Bacterial input was $0.5-1 \times 10^7$ CFU ml$^{-1}$. Data are means±s.d. of triplicate cultures and represent two or three independent experiments. In some panels, error bars are too small to be seen.

FIG. 2A is a graph showing the $pH_{IB}$ of wildtype Mtb (H37RV) and five-acid sensitive mutants measured at two extracellular pHs ($pH_{EX}$) in pcit-Ty buffer: $pH_{EX}$ of 7.4 and 4.5 after incubation for the indicated times. In FIG. 2B, $pH_{IB}$ was measured in wildtype Mtb and the Rv2136c and Rv3671c mutants after incubation for the indicated times in pcit-Ty buffer at an extracellular pH of 4.5. $pH_{IB}$ measurements at 8 h for wild-type Mtb, Rv3671c mutant, and complemented mutant (Rv3671c COMP) in pcit-Ty-4.5 are shown in the graph of FIG. 2C. FIG. 2D is a graph showing quantification of CFU after 6 days of culturing wild-type Mtb, Rv3671c mutant, complemented mutant, and mutant complemented with Flag-tagged wild-type Rv3671c (WT) or S343A Rv3671c in pcit-Ty-4.5. FIG. 2E are immunoblots of cytosol and cell envelope fractions of the wild-type Mtb, Rv3671c mutant, and mutant complemented with Flag-tagged wild-type Rv3671c (WT) or S343A Rv3671c probed with a Flag-specific antibody (Anti-Flag). An immunoblot for dihydrolipoamide S-acyltransferase (Anti-DLAT) serves as a loading control. Data are means±s.d. of three experiments, each in triplicate in FIGS. 2A and 2C; data are means±s.d. of triplicate cultures and represent two or three independent experiments in FIGS. 2B, 2D and 2E FIGS. 3A-H demonstrate that the Rv3671c mutant fails to maintain $pH_{IB}$ and is killed within activated macrophages.

FIG. 6 is an amino acid sequence alignment showing the conserved catalytic residues of serine proteases found in Rv3671c. Amino acid sequence alignment of protease domains of Mtb Rv3671c with experimentally confirmed serine proteases: human trypsin-2, human neutrophil elastase, and *Escherichia coli* degP/HtrA. Conserved active site histidine, aspartate and serine residues are indicated by asterisks and shading indicates identical residues.

FIG. 9B shows the survival of wild-type Mtb (H37Rv) and the Rv3671c mutant in pcit-Ty-4.5 after addition of the vehicle control DMSO, CCCP or monensin. Data are means±s.d. of triplicate cultures and represent two independent experiments. The limit of detection is 100 CFU/ml. DMSO concentration was 0.1%. CCCP and monensin have been previously used to dissipate $pH_{IB}$ and decrease viability of *M. smegmatins* and *M. bovis* BCG in acidified medium (Rao et al., "Intracellular pH Regulation by *Mycobacterium Smegmatis* and *Mycobacterium Bovis* BCG," *Microbiology* 147, 1017-24 (2001), which is hereby incorporated by reference in its entirety).

In FIG. 10B colony morphology (left) and cording (right) are shown. For TEM and SEM samples were fixed with 2.5% glutaraldehyde, 4% paraformaldehyde, 0.02% picric acid in sodium cacodylate 0.1 M buffer for 4 hours prior to removal from the BSL3 containment facility. Samples were then treated with 1% OsO4-1.5% K-ferricyanide for 60 minutes and 1.5% uranyl acetate for 30 minutes. A series of ethanol dehydrations were performed followed by absolute acetone. For TEM, samples in Spurr's resin were sectioned, contrasted with lead citrate and viewed on a JSM 100 CX-II electron microscope. For SEM, samples were dried through $CO_2$, sputter coated with gold-palladium and viewed on a FEI Quanta 600 electron microscope. Colonies were visualized 2-3 weeks after plating on 7H11 agar. To visualize cording Mtb strains were grown in supplemented 7H9 without Tween 80 and stained with TB Stain Kit (Becton Dickinson).

FIGS. 13A-13B are calibration curves of pHGFP. FIG. 13A is a calibration curve for in vitro $pH_{IB}$ measurements on Mtb. For measurements, 100 µL of the pcit buffer series containing lysate were read in triplicate in a plate reader at excitations of 395 nm and 475 nm and an emission of 510 nm. FIG. 13B is a calibration curve for intraphagosomal $pH_{IB}$ measurements on Mtb. For measurements, 100 µL of the pcit buffer series containing lysate were placed in glass bottom dishes used for cell microscopy and 5 images at excitations of 410 nm and 470 nm were taken. Calibration curves were generated by placing 100 µg of lysate (at a concentration of 20 µg/µl) prepared from wild-type Mtb (H37Rv) transformed with Psmyc-pHGFP in 100 µL of a pcit buffer series at pH 5.5 to pH 8.5 in 0.5 pH increments. The 395/475 or 410/470 fluorescence ratios were fitted to pH with the sigmoidal Hill equation using Prism Software (GraphPad Prism 4.0). Data shown are means±s.d.

FIG. 14 is a table showing the twenty-one identified Mtb mutants that are hypersensitive to 7H9-Tw-4.5. Transposon mutants were exposed in the screen to 7H9-Tween at pH 4.5 as described infra. Mutants that reached an $OD_{580}$<0.1 while wild-type H37Rv was at an $OD_{580}$ 0.8-1.0 were marked as being hypersensitive to 7H9-Tw-4.5. (^) Annotations regarding the name, description, and function of the transposon mutant are from TubercuList (Cole et al., "Deciphering the Biology of *Mycobacterium Tuberculosis* from the Complete Genome Sequence," *Nature* 393:537-44 (1998), which is hereby incorporated by reference in its entirety). (+) Mutants were determined to be sensitive to 7H9-Ty at pH 4.5 as described infra. Mutants exhibiting less than 40% survival were labeled as being hypersensitive. Percent survival was calculated by dividing the number of bacteria remaining at day 6 by the amount that were added at the start of the experiment. (#) The five mutants that were sensitive in 7H9-Ty at pH 4.5 (and the mutants pbpA, Rv3679, Rv0007, Rv0955, mpa) were tested for sensitivity to pcit-Ty buffer at pH 4.5 as described infra. Mutants exhibiting less than 40% survival were labeled as being hypersensitive. Percent survival was calculated by dividing the number of bacteria remaining at day 6 by the amount that were added at the start of the experiment. **Not tested

DETAILED DESCRIPTION OF THE INVENTION

Figures 1A, 1B, 1C, 1D:
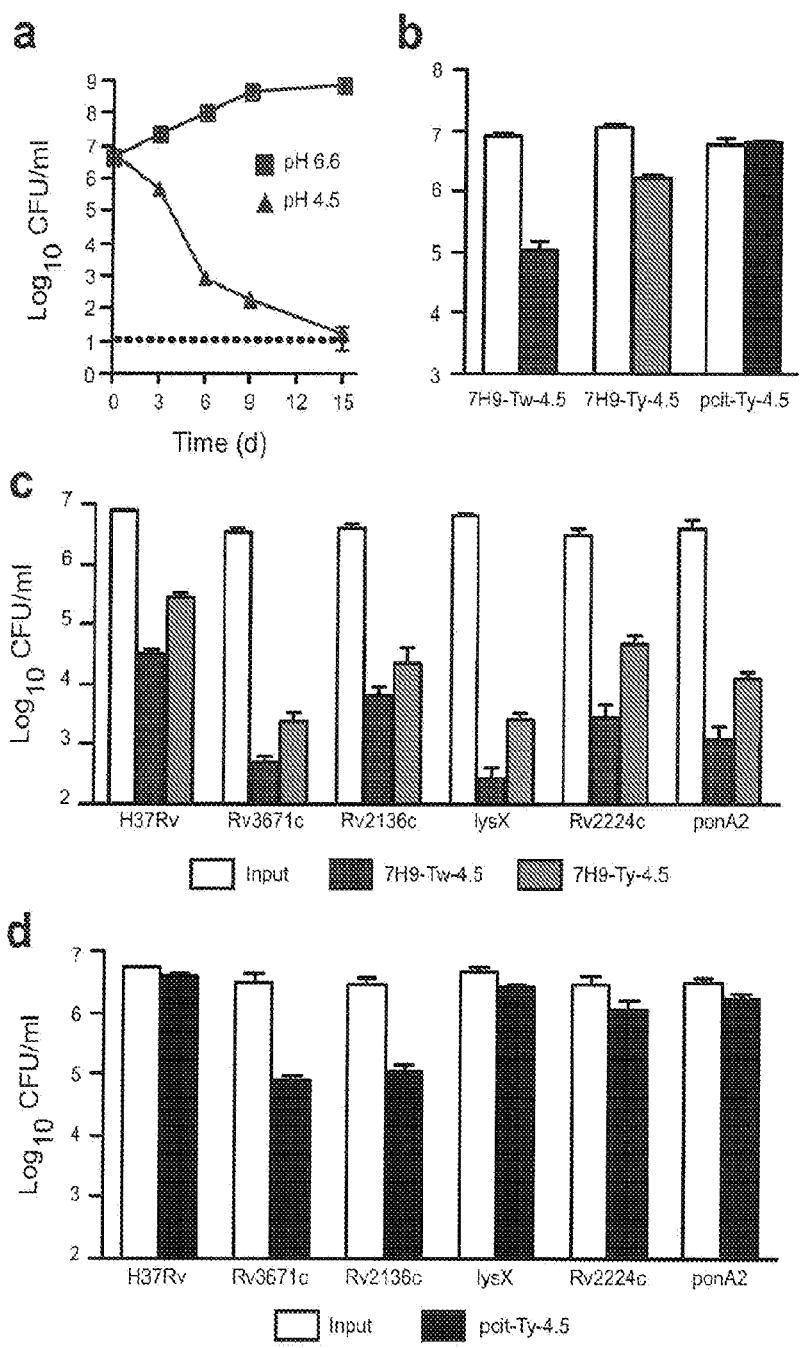
FIGS. 1A-1D show the survival of wild-type Mtb and transposon mutants at pH 4.5.

A first aspect of the present invention is directed to a method of inhibiting the growth of bacteria. This method involves exposing the bacteria to an agent that disrupts intrabacterial pH homeostasis under conditions effective to inhibit the growth of the bacteria.

As used herein, inhibiting the growth of bacteria encompasses slowing bacterial growth or halting bacterial growth. In a preferred embodiment of the present invention, inhibiting growth of the bacteria includes killing of the bacteria.

In accordance with this aspect of the present invention, exposure of the bacteria to an agent that disrupts intrabacterial pH homeostasis is carried out under pH conditions that are different than the homeostatic intrabacterial pH conditions of the bacteria. More preferably, the exposure is carried out under pH conditions that become intolerable to bacterial growth and survival as a result of exposure to the agent. In one embodiment, exposure of the bacteria to an agent that disrupts intrabacterial pH homeostasis is carried out under conditions that are acidic to the bacteria (e.g., pH<7.0). Such acidic pH conditions exist, for example, within the stomach or phagolysosomes of activated macrophages of a bacterial host.

The method of the present invention can be used to inhibit the growth of any bacteria, particularly bacteria having an endogenous mechanism of maintaining and/or adjusting internal pH independently of the external environmental pH conditions. For example, many enteric bacteria have developed acid tolerance for survival in the acidic conditions of the stomach. Acid tolerance can be important for survival and is believed to be important for virulence of many strains of bacteria. Accordingly, the method of the present invention can be used to inhibit the growth of any bacteria having developed a tolerance to variations of external pH conditions. In a preferred embodiment, the method of the present invention is used to inhibit the growth of any species of Mycobacterium. Exemplary species of Mycobacterium include, without limitation, Mycobacterium tuberculosis, Mycobacterium avium-intracellulare, Mycobacterium kansasii, Mycobacterium bovis, Mycobacterium bovis BCG, Mycobacterium africanum, Mycobacterium canetti, Mycobacterium caprae, Mycobacterium pinnipedii, Mycobacterium ulcerans, Mycobacterium leprae.

As described herein, applicants have discovered that the Rv3671c gene in Mycobacterium tuberculosis is required for acid tolerance and survival in the acidic conditions encountered during infection of the subject. Rv3671c encodes a membrane associated serine hydrolase that is essential for pH maintenance and intracellular survival of Mtb. Disruption of Rv3671c serine hydrolase activity causes a loss of intrabacterial pH homeostasis, resulting in an inhibition of bacterial growth and survival in vitro and during in vivo infection of a host animal. Accordingly, suitable agents of the present invention for disrupting intrabacterial homeostasis include serine hydrolase inhibitors. Preferred agents of the present invention are serine hydrolase inhibitors that specifically inhibit the serine hydrolase activity of the Rv3671c gene product or its homolog in other bacterial strains, particularly Mycobacterium strains. Inhibition of Rv3671c serine hydrolase activity can be achieved via inhibition of Rv3671c gene expression, protein synthesis or expression, or enzymatic activity. Methods of identifying compounds and agents that inhibit intrabacterial homeostasis, possibly through inhibition of the Rv3671 pathway, are described herein. Inhibitors of intrabacterial pH homeostasis, including potential inhibitors of the Rv3671c pathway that have been identified to date and are suitable for use in the methods of the present invention are shown in Table 1 below.

TABLE 1

Inhibitors of $pH_{IB}$ Homeostasis

| Structure | CA Index Name |
|---|---|
| 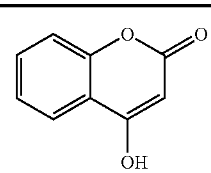 | 4-hydroxy-2H-chromen-2-one |

TABLE 1-continued

Inhibitors of pH$_{IB}$ Homeostasis

| Structure | CA Index Name |
|---|---|
| 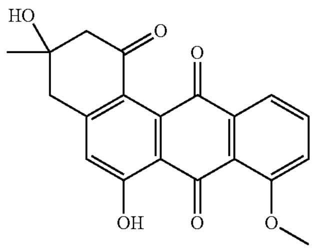 | 3,6-dihydroxy-8-methoxy-3-methyl-3,4-dihydrotetraphene-1,7,12(2H)-trione |
| | (E)-6-(but-2-en-2-yl)-2,4,7-trichloro-3,8-dihydroxy-1,9-dimethyl-11H-dibenzo[b,e][1,4]dioxepin-11-one |
| 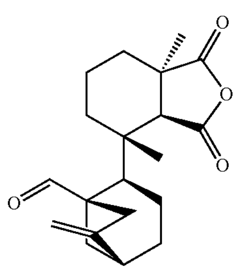 [SMILES: C=C1C[C@]2(C=O)C[C@H]1CC[C@@H]2[C@]1(C)CCC[C@@]2(C)C(=O)OC(=O)[C@@H]12] | (1R,2R,5R)-2-((3aS,4S,7aR)-4,7a-dimethyl-1,3-dioxooctahydroisobenzofuran-4-yl)-6-methylenebicyclo[3.2.1]octane-1-carbaldehyde |
| 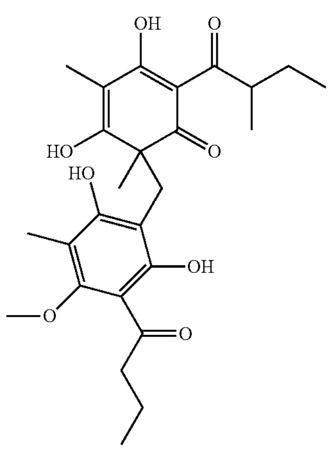 [SMILES: CCCC(=O)c1c(O)c(CC2(C)C(=O)C(C(=O)C(C)CC)=C(O)C(C)=C2O)c(O)c(C)c1OC] | 6-(3-butyryl-2,6-dihydroxy-4-methoxy-5-methylbenzyl)-3,5-dihydroxy-4,6-dimethyl-2-(2-methylbutanoyl)cyclohexa-2,4-dienone |
| 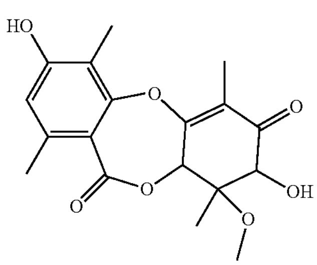 [SMILES: COC1(C)C(O)C(=O)C(C)=C2Oc3c(C)c(O)cc(C)c3C(=O)OC21] | 3,8-dihydroxy-9-methoxy-1,4,6,9-tetramethyl-9,9a-dihydro-7H-dibenzo[b,e][1,4]dioxepine-7,11 (8H)-dione |

TABLE 1-continued

Inhibitors of pH$_{IB}$ Homeostasis

| Structure | CA Index Name |
|---|---|
| 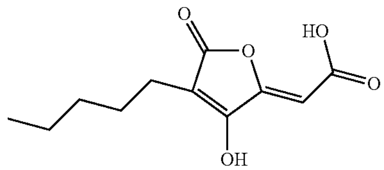 [SMILES: CCCCCC1=C(O)/C(=C/C(=O)O)OC1=O] | (Z)-2-(3-hydroxy-5-oxo-4-pentylfuran-2(5H)-ylidene)acetic acid |
| 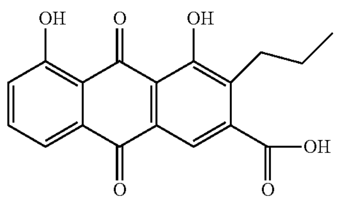 [SMILES: CCCc1c(C(=O)O)cc2c(c1O)C(=O)c1c(O)cccc1C2=O] | 4,5-dihydroxy-9,10-dioxo-3-propyl-9,10-dihydroanthracene-2-carboxylic acid |
| 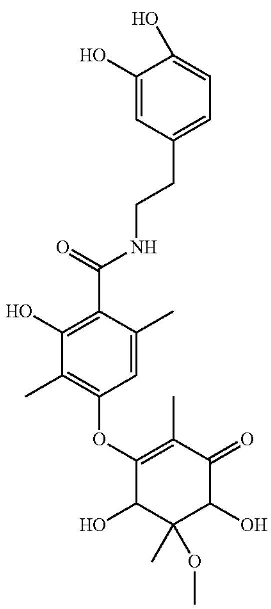 [SMILES: COC1(C)C(O)C(=O)C(C)=C(Oc2cc(C)c(C(=O)NCCc3ccc(O)c(O)c3)c(O)c2C)C1O] | 4-(4,6-dihydroxy-5-methoxy-2,5-dimethyl-3-oxocyclohex-1-enyloxy)-N-(3,4-dihydroxyphenethyl)-2-hydroxy-3,6-dimethylbenzamide |
| 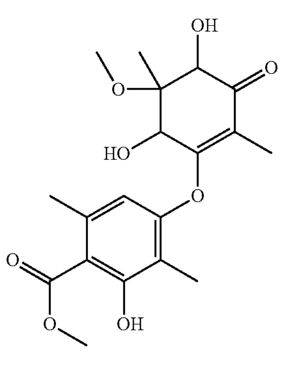 [SMILES: COC(=O)c1c(C)cc(OC2=C(C)C(=O)C(O)C(C)(OC)C2O)c(C)c1O] | Methyl 4-(4,6-dihydroxy-5-methoxy-2,5-dimethyl-3-oxocyclohex-1-enyloxy)-2-hydroxy-3,6-dimethylbenzoate |

TABLE 1-continued

Inhibitors of pH$_{IB}$ Homeostasis

| Structure | CA Index Name |
|---|---|
| 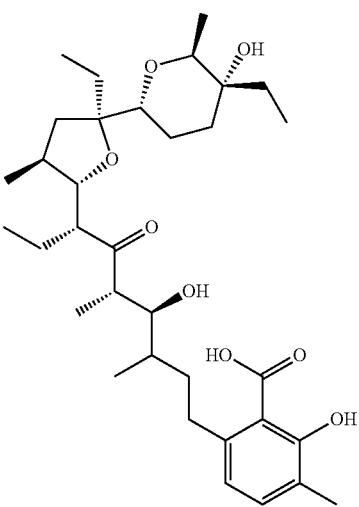 [SMILES: CC[C@@H](C(=O)[C@@H](C)[C@@H](O)C(C)CCc1ccc(C)c(O)c1C(=O)O)[C@H]1O[C@](CC)([C@H]2CC[C@](O)(CC)[C@H](C)O2)C[C@@H]1C] | 6-((4S,5S,7R)-7-((2S,3S,5S)-5-ethyl-5-((2R,5R,6S)-5-ethyl-5-hydroxy-6-methyltetrahydro-2H-pyran-2-yl)-3-methyltetrahydrofuran-2-yl)-4-hydroxy-3,5-dimethyl-6-oxononyl)-2-hydroxy-3-methylbenzoic acid |
| 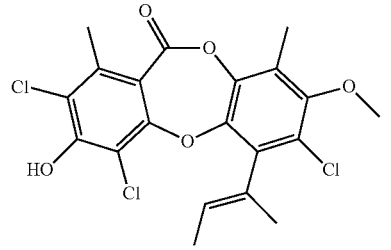 [SMILES: C/C=C(\C)c1c(Cl)c(OC)c(C)c2c1Oc1c(Cl)c(O)c(Cl)c(C)c1C(=O)O2] | (E)-6-(but-2-en-2-yl)-2,4,7-trichloro-3-hydroxy-8-methoxy-1,9-dimethyl-11H-dibenzo[b,e][1,4]dioxepin-11-one |
| 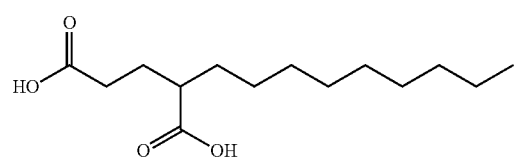 [SMILES: CCCCCCCCCC(CCC(=O)O)C(=O)O] | 2-nonylpentanedioic acid |
| 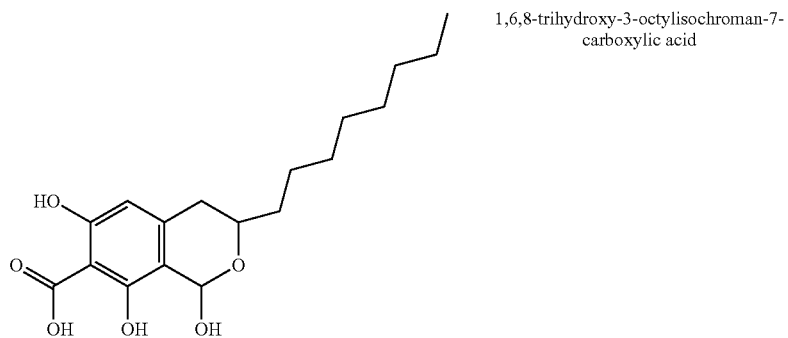 | 1,6,8-trihydroxy-3-octylisochroman-7-carboxylic acid |

TABLE 1-continued

Inhibitors of $pH_{IB}$ Homeostasis

| Structure | CA Index Name |
|---|---|
| 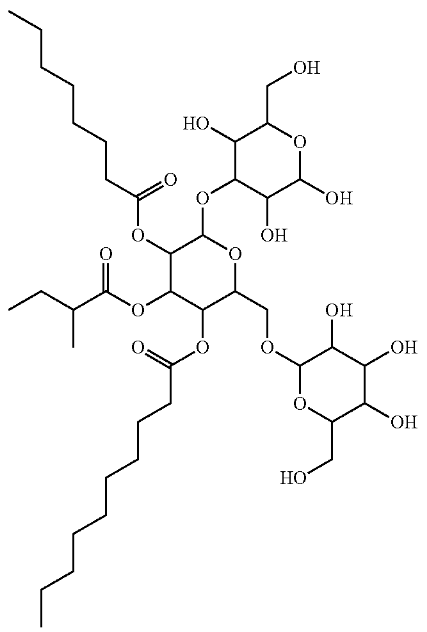 [SMILES: CCCCCCCCCC(=O)OC1C(COC2OC(CO)C(O)C(O)C2O)OC(OC2C(O)C(O)OC(CO)C2O)C(OC(=O)CCCCCCC)C1OC(=O)C(C)CC] | 4-(2-methylbutanoyloxy)-5-(octanoyloxy)-2-((3,4,5-trihydroxy-6-(hydroxymethyl)tetrahydro-2H-pyran-2-yloxy)methyl)-6-(2,3,5-trihydroxy-6-(hydroxymethyl)tetrahydro-2H-pyran-4-yloxy)tetrahydro-2H-pyran-3-yl decanoate |
| 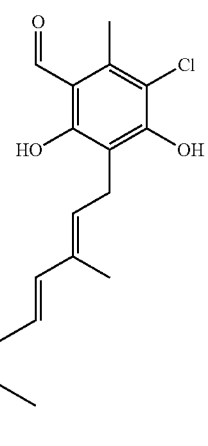 | 3-chloro-4,6-dihydroxy-2-methyl-5-((2E,4E)-3-methyl-5-(1,2,6-trimethyl-5-oxocyclohex-3-enyl)penta-2,4-dienyl)benzaldehyde |
| 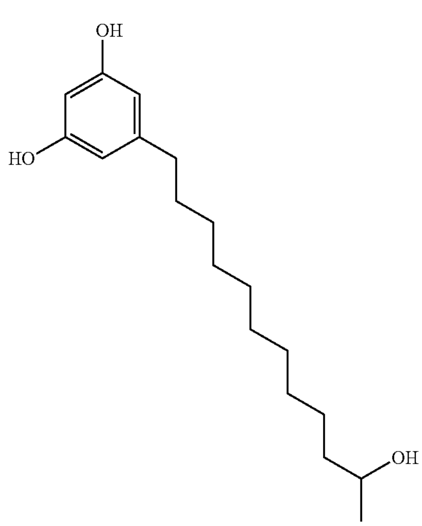 [SMILES: CC(O)CCCCCCCCCCc1cc(O)cc(O)c1] | 5-(13-hydroxytetradecyl)benzene-1,3-diol |

TABLE 1-continued

Inhibitors of pH$_{IB}$ Homeostasis

| Structure | CA Index Name |
|---|---|
| 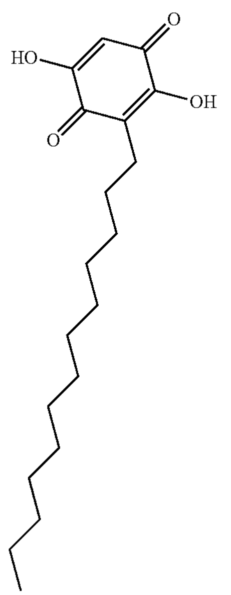 [SMILES: CCCCCCCCCCCCCC1=C(O)C(=O)C=C(O)C1=O] | 2,5-dihydroxy-3-tridecylcyclohexa-2,5-diene-1,4-dione |
| 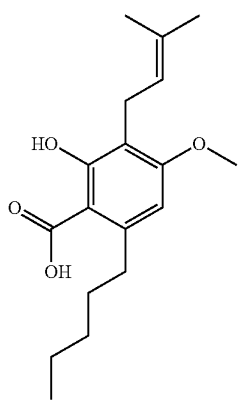 [SMILES: CCCCCc1cc(OC)c(CC=C(C)C)c(O)c1C(=O)O] | 2-hydroxy-4-methoxy-3-(3-methylbut-2-enyl)-6-pentylbenzoic acid |
| 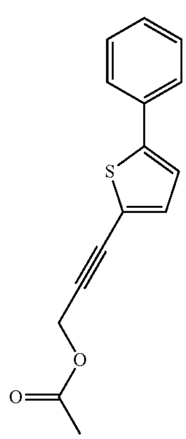 [SMILES: CC(=O)OCC#Cc1ccc(-c2ccccc2)s1] | 3-(5-phenylthiophen-2-yl)prop-2-ynyl acetate |

TABLE 1-continued

Inhibitors of $pH_{IB}$ Homeostasis

| Structure | CA Index Name |
|---|---|
| 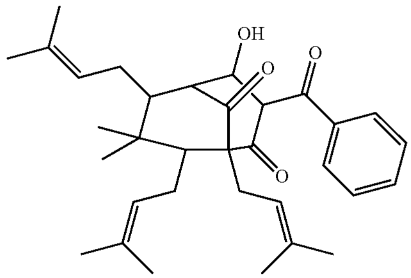 [SMILES: CC(C)=CCC1C2C(=O)C(CC=C(C)C)(C(=O)C(C(=O)c3ccccc3)C2O)C(CC=C(C)C)C1(C)C] | Bicyclo[3.3.1]nonane-2,4,9-trione,3-(hydroxyphenylmethylene)-6,6-dimethyl-1,5,7-tris(3-methyl-2-buten-1-yl), (1R,3E,5S,7R) |
| 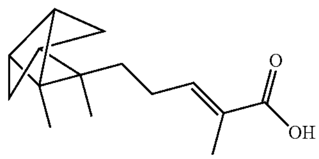 [SMILES: C/C(=C\CCC1(C)C2CC3C(C2)C31C)C(=O)O] | 2-Pentenoic acid, 5-[(1R,3R,6S)-2,3-dimethyltricyclo[2.2.1.02,6]hept-3-yl]-2-methyl-,(2E)-(9CI) |
| 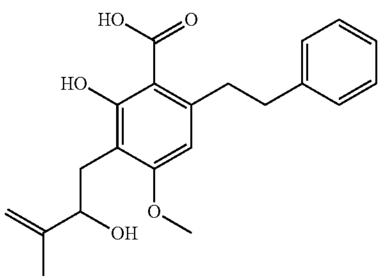 [SMILES: C=C(C)C(O)Cc1c(OC)cc(CCc2ccccc2)c(C(=O)O)c1O] | 2-hydroxy-3-(2-hydroxy-3-methylbut-3-enyl)-4-methoxy-6-phenethylbenzoic acid |
| 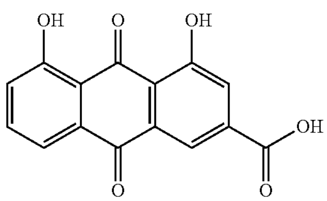 [SMILES: O=C(O)c1cc(O)c2c(c1)C(=O)c1cccc(O)c1C2=O] | 4,5-dihydroxy-9,10-dioxo-9,10-dihydroanthracene-2-carboxylic acid |

In a preferred embodiment of the present invention, the agent that inhibits intrabacterial pH is selected from the group consisting of 6-(3-butyryl-2,6-dihydroxy-4-methoxy-5-methylbenzyl)-3,5-dihydroxy-4,6-dimethyl-2-(2-methylbutanoyl)cyclohexa-2,4-dienone; (Z)-2-(3-hydroxy-5-oxo-4-pentylfuran-2(5H)-ylidene)acetic acid; 4-(2-methylbutanoyloxy)-5-(octanoyloxy)-2-((3,4,5-trihydroxy-6-(hydroxymethyl)tetrahydro-2H-pyran-2-yloxy)methyl)-6-(2,3,5-trihydroxy-6-(hydroxymethyl)tetrahydro-2H-pyran-4-yloxy)tetrahydro-2H-pyran-3-yl decanoate; 2-hydroxy-4-methoxy-3-(3-methylbut-2-enyl)-6-pentylbenzoic acid; and 2-hydroxy-3-(2-hydroxy-3-methylbut-3-enyl)-4-methoxy-6-phenethylbenzoic acid.

A second aspect of the present invention is directed to a method of treating a bacterial infection in a subject. This method involves administering to the subject an agent that disrupts intrabacterial pH homeostasis under conditions effective to treat the bacterial infection. In accordance with this aspect of the present invention, a subject having a bacteria infection is selected prior to administering an agent that disrupts intrabacterial pH homeostasis.

As used herein, the treatment of a bacterial infection includes, without limitation, slowing bacterial growth of the infection, halting bacterial growth of the infection, killing the bacteria, and/or eliminating the bacterial infection.

As used herein, "subject" refers to any animal having a bacterial infection that is amenable to treatment in accordance with the methods of the present invention. Preferably, the subject is a mammal. Exemplary mammalian subjects include, without limitation, humans, non-human primates, dogs, cats, rodents (e.g., mouse, rat, guinea pig), horses, cattle, sheep, and pigs.

Any subject having a bacterial infection is suitable for treatment in accordance with the methods of the present invention. More preferably, the subject is inflicted with a bacterial infection caused by any species of *Mycobacterium*, including, but not limited to, *M. tuberculosis, M. avium-intracellulare, M. kansasii, M. bovis, M. bovis* BCG, *M. africanum, M. canetti, M. caprae, M. pinnipedii, M. ulcerans, M. leprae*. In a preferred embodiment of the present invention, the subject has a *M. tuberculosis* infection.

Suitable agents for treating a subject having a bacterial infection include serine hydrolase inhibitors. Preferably, the serine hydrolase inhibitor is one that is specific for the inhibition of the serine hydrolase activity of the Rv3671c gene product or a homolog thereof. Suitable agents include those agents that inhibit Rv3671c gene expression, protein synthesis or expression, or enzymatic activity. Exemplary agents of the present invention are shown in Table 1 supra.

In a preferred embodiment of the present invention, the agent is formulated into a pharmaceutical composition that is suitable for administration to the subject. Suitable pharmaceutical compositions typically include the therapeutic agent, in this case an agent of Table 1, and a pharmaceutically acceptable carrier. Acceptable pharmaceutical carriers include solutions, suspensions, emulsions, excipients, powders, or stabilizers.

The agents or pharmaceutical composition containing the agents of the present invention can be administered by any means suitable for producing the desired therapeutic endpoint, i.e., inhibition of bacterial growth and survival. Delivery can be carried out via systemic approaches or directly to a site of infection. Suitable delivery routes include oral, by inhalation, by intranasal instillation, topically, transdermally, parenterally, subcutaneously, intravenous injection, intra-arterial injection, intramuscular injection, intraplurally, intraperitoneally, or by application to mucous membrane. The agent or composition can be delivered repeatedly over a course of time to achieve an optimal therapeutic response. The composition or agent can also be delivered in combination with, prior to, or after the delivery of one or more other therapeutic or antibiotic agents.

Direct administration to the lungs is a preferred method for treating Mycobacterial infections, such as tuberculosis. Accordingly, the agents or compositions of the present invention may be administered via aspiration, airway instillation, aerosolization, nebulization, intranasal instillation, oral or nasogastic instillation. Suitable formulations for such administration can be manufactured using standard techniques known in the art, and administered using, for example, a metered-dose inhaler, updraft nebulization, or other means known in the art. Alternatively, the agents can be delivered using intranasal microparticle resins (Takenaga et al., "Microparticle Resins as a Potential Nasal Drug Delivery System for Insulin," *J Controlled Release* 52:81-87 (1998), which is hereby incorporated by reference in its entirety) or lysophosphatidyl-glycerol compounds (see e.g., U.S. Pat. No. 5,725,871 to Illum et al., which is hereby incorporated by reference in its entirety). Likewise, transmucosal drug delivery in the form of a polytetrafluoroetheylene support matrix can also be utilized as described in U.S. Pat. No. 5,780,045 to McQuinn et al., which is hereby incorporated by reference in its entirety.

As an alternative to direct administration to the lungs, the therapeutic agents of the present invention can be formulated for injectable use (i.e., intravenous, intra-arterial, intramuscular administration). Such formulations may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

In certain applications, the agents disclosed herein may be formulated into compositions for oral administration to a subject. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like (see, e.g., Mathiowitz et al., "Biologically Erodable Microspheres as Potential Oral Drug Delivery Systems," *Nature* 386:410-414 (1997); Hwang et al., "Gastric Retentive Drug-Delivery Systems," *Crit. Rev Ther Drug Carrier Syst* 15:243-84 (1998); U.S. Pat. No. 5,641,515 to Ramtoola; U.S. Pat. No. 5,580,579 to Ruddy et al.; and U.S. Pat. No. 5,792,451 to Sarubbi et al., which are hereby incorporated by reference in their entirety). The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient(s) may be varied and may be between about 1 or 2% and about 60% or 70% or more of the weight or volume of the total formulation. Naturally, the amount of active compound(s) in each therapeutically useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

As is known in the art, because orally administered agents need to survive the digestive system before cellular uptake, it is possible to administer the therapeutic agents of the present invention with any of a variety of stabilizing reagent that inhibits destruction thereof. One such type of stabilizing reagent is an enteric coating.

The agents of the present invention may also be delivered using liposomes, nanocapsules, microparticles, microspheres, lipid particles, vesicles, and the like. In particular, the compositions of the present invention may be formulated for delivery either encapsulated in a lipid particle, a liposome, a vesicle, a nanosphere, or a nanoparticle.

The formation and use of liposomes is generally known to those of skill in the art (see e.g., Couvreur et al., "Nanocapsules: A New Type of Lysosomotropic Carrier," *FEBS Lett.* 84(2):323-326 (1977); Couvreur (1988); Lasic D., "Novel Applications of Liposomes," *Trends Biotechnol.* 16(7):307-321 (1998), which are hereby incorporated by reference in their entirety and describe the use of liposomes and nanocapsules in the targeted antibiotic therapy for intracellular bacterial infections and diseases). Recently, liposomes were developed with improved serum stability and circulation half-life (Gabizon and Papahadjopoulos, "Liposome Formulations with Prolonged Circulation Time in Blood and Enhanced Uptake by Tumors," *Proc Natl Acad Sci USA.* 85(18):6949-6953 (1988) and U.S. Pat. No. 5,741,516 to Webb et al., which are hereby incorporated by reference in their entirety). Further, various methods of liposome and liposome like preparations as potential drug carriers have been reviewed (Margalit, "Liposome-Mediated Drug Targeting in Topical and Regional Therapies," *Crit. Rev Ther Drug Carrier Syst.* 12(2-3):233-261 (1995); U.S. Pat. No. 5,567,434 to Szoka; U.S. Pat. No. 5,552,157 to Yagi; U.S. Pat. No. 5,565,213 to Nakamori; U.S. Pat. No. 5,738,868 to Shinkarenko; and U.S. Pat. No. 5,795,587 to Gao, which are hereby incorporated by reference in their entirety).

Effective amounts of the agents or pharmaceutical composition of the present invention will depend upon the mode of administration, frequency of administration, nature of the treatment, age, and condition of the individual to be treated, and the type of pharmaceutical composition used to deliver the therapeutic agent. Effective levels of the composition may range from about 0.001 to about 2.5 mg/kg depending upon the clinical endpoints and toxicity thresholds. While individual doses may vary, optimal ranges of the effective amounts may be determined by one of ordinary skill in the art.

The pharmaceutical composition containing the therapeutic agent or the therapeutic agent itself can be administered to a patient alone or in combination with any other standard therapy, including one or more antibacterial agents, to treat the bacterial infection. For example, anti-tuberculosis chemotherapy currently involves administration of one or more (and frequently three or more) antibiotics such as isoniazid, rifampin, ethambutol, rifapentine, p-aminosalicylic acid, pyrazinamide, streptomyxin, capreomycin, cycloserine, ethionamide, aminoglycosides (e.g., amikacin and kanamycin), amithiozone, rifabutin, clofazimine, arithromycin, clarithromycin, fluoroquinolones (e.g., ciprofloxacin, moxifloxacin, levofloxacin, and ofloxacin). The agents of the present invention can be administered in combination with any one or more of the above anti-bacterial agents commonly administered to a subject having a *M. tuberculosis* infection.

The present invention also includes the use of other agents that are shown to disrupt intracellular pH homeostasis, including those that inhibit the Rv3671c pathway. Such compounds can be identified by suitable screening assays. Thus, another aspect of the present invention is directed to a method of identifying a compound that interferes with intracellular pH homeostasis of a pathogen. This method involves providing one or more candidate compounds and providing a pathogen, where the pathogen has a detectable indicator of intracellular pH. The method further involves contacting the one or more candidate compounds with the pathogen and detecting the intracellular pH of the pathogen. Detecting a change in the intracellular pH in the presence of a candidate compound identifies a compound that interferes with the intracellular pH homeostasis of the pathogen.

In accordance with this aspect of the invention, suitable pathogens for use in the screening method of the present invention include, but are not limited to, bacterial, fungal, and viral pathogens. In one embodiment of the present invention, the pathogen is a bacteria. Suitable bacteria include, without limitation, any species of *Mycobacterium* (e.g., *M. tuberculosis, M. avium-intracellulare, M. kansasii, M. bovis, M. bovis* BCG, *M. africanum, M. canetti, M. caprae, M. pinnipedii, M. ulcerans, M. leprae*). In a preferred embodiment of the present invention, the pathogen is *M. tuberculosis*.

The screening method of the present invention employs the use of a pathogen having a detectable indicator of intracellular pH. Suitable detectable indicators of intracellular pH are known in the art and include, for example, cell permeate seminaphthorhodafluors (SNARF dyes), 2'-7'-bis(carboxyethyl)-5(6)-carboxyfluorescein (BCECF), LysoSensor Probes, and other commercially available pH indicators designed for tracking pH in biological systems (Molecular Probes/Invitrogen, Carlsbad, Calif.). In a preferred embodiment of the present invention the detectable indicator of intracellular pH is a pH sensitive Green Fluorescent Protein (pH-GFP) as described in U.S. Pat. No. 6,670,449 to Miesenbock et al., which is hereby incorporated by reference in its entirety. The ratiometric pH-GFP used herein was obtained by introducing specific amino acid substitutions to the chromophore that cause the resulting protein to alter its excitation spectrum according to the pH of the surrounding environment (Miesenböck et al., "Visualizing Secretion and Synaptic Transmission with pH-sensitive Green Fluorescent Proteins," *Nature* 394:192-195 (1998), which is hereby incorporated by reference in its entirety). Expressing the ratiometric GFP or other pH sensitive protein indicators in the pathogen of interest can be achieved as described infra or using molecular cloning techniques readily known in the art. Exemplary procedures are described in SAMBROOK & RUSSELL, MOLECULAR CLONING: A LABORATORY MANUAL (2d ed. 1989), which is hereby incorporated by reference in its entirety. The gene encoding the ratiometric GFP used herein (GenBank Accession No. AF058694) can be readily amplified using known primers (Olsen et al., "Noninvasive Measurement of Bacterial Intracellular pH on a Single Cell Level with Green Fluorescent Protein and Fluorescence Ratio Imaging Microscopy," *Appl. Environ. Microbiol.* 68(8):4145-47 (2002), which is hereby incorporated by reference in its entirety) and inserted into a suitable expression vector. Suitable expression vectors include, but are not limited to, viral vectors such as lambda vector system gt11, gtWES.tB, Charon 4, and plasmid vectors such as pCMV, pBR322, pBR325, pACYC177, pACYC184, pUC8, pUC9, pUC18, pUC19, pLG339, pR290, pKC37, pKC101, SV 40, pBluescript II, pQE, pIH821, pGEX, pET series, and any derivatives thereof. Any appropriate vectors now known or later described for genetic transformation are suitable for use with the present invention. The expression vector can be introduced into the pathogen of interest via transfection, transduction, or electroporation techniques readily known in the art.

In accordance with this aspect of the present invention and as described infra in Example 11, the candidate compounds are contacted with a pathogen under pH conditions that are different than that of the intracellular homeostatic pH conditions of the pathogen. In a preferred embodiment, the candidate compound is contacted with the pathogen under acidic pH conditions (i.e., pH<7.0). Alternatively, the candidate compound is contacted with the pathogen under alkaline pH conditions (i.e., pH>7.5). Under these conditions, a compound that alters the intracellular pH of the pathogen, is a compound that interferes with the pathogen's mechanism of maintaining intracellular pH.

The intracellular pH indicator of the pathogen can be detected using fluorescent microscopy, confocal laser-scanning microscopy, flow cytometry, microplate spectrofluorometer or luminometer, or other methods known in the art. As described herein, the ratiometric pH-GFP is detected using an excitation and emission spectra of 395/510 nm and 510/475 nm. The ratio of both readings is taken and converted to an intracellular pH level using a reference standard curve.

EXAMPLES

The present invention is further described with reference to the following examples, which are not intended to limit the scope of the claimed invention in any way.

Example 1

Strains and Media

Mtb was grown in Middlebrook 7H9 medium containing 0.2% glycerol, 0.5% BSA, 0.2% dextrose, 0.085% NaCl and 0.05% Tween-80 (7H9-Tw) or 0.02% Tyloxapol (7H9-Ty), or on Middlebrook 7H10 or 7H11 agar containing 10% oleic acid-albumin-dextrose-catalase. The Rv3671c mutant showed reduced growth on 7H11 agar and was cultured on 7H10 agar. 7H9-Tw and 7H9-Ty were acidified to pH 4.5 with 2 N HCl and phosphate-citrate (pcit) buffers were prepared from 200 mM sodium phosphate and 100 mM citric acid.

Example 2

Mtb Mutant Screen

The φ MycoMarT7 transposon mutants (Darwin et al., "The Proteasome of *Mycobacterium Tuberculosis* is Required for Resistance to Nitric Oxide," *Science* 302:1963-1966 (2003), which is hereby incorporated by reference in its entirety) were grown in 96-well plates to stationary phase in 7H9-Tw-6.6 medium. Aliquots (5 µl) were diluted 40-fold in 7H9-Tw-4.5 medium to ~$5 \times 10^6$ CFU·ml$^{-1}$. After 6 days, the mutants were subcultured 10-µl aliquots in 200 µl 7H9-Tw-6.6 medium. Optical densities were measured at an absorbance of 580 nm ($OD_{580}$) 2-3 weeks later, when wild-type Mtb reached $OD_{580}$~0.8-1.0, and rescreened mutants with $OD_{580}$<0.1 five times. Chromosomal DNA was analyzed from colony-purified mutants by Southern blotting with the kanamycin gene as a probe to confirm single transposon insertions, and the insertion sites were sequenced.

Example 3

Measurement of Acid Sensitivity

Early-log-phase cultures were washed with 7H9-Tw-4.5, 7H9-Ty-4.5, or pcit-Ty-4.5 medium and centrifuged at 120 g for 10 min. Single-cell suspensions were adjusted to ~$5 \times 10^6$ CFU·ml$^{-1}$ in 7H9-Tw-4.5, 7H9-Ty-4.5, or pcit-Ty-4.5 medium and incubated at 37° C. CFU was determined by plating serial dilutions of the suspensions on 7H10 or 7H11 agar plates.

Example 4

Figures 3A, 3B, 3C, 3D, 3E, 3F, 3G, 3H:
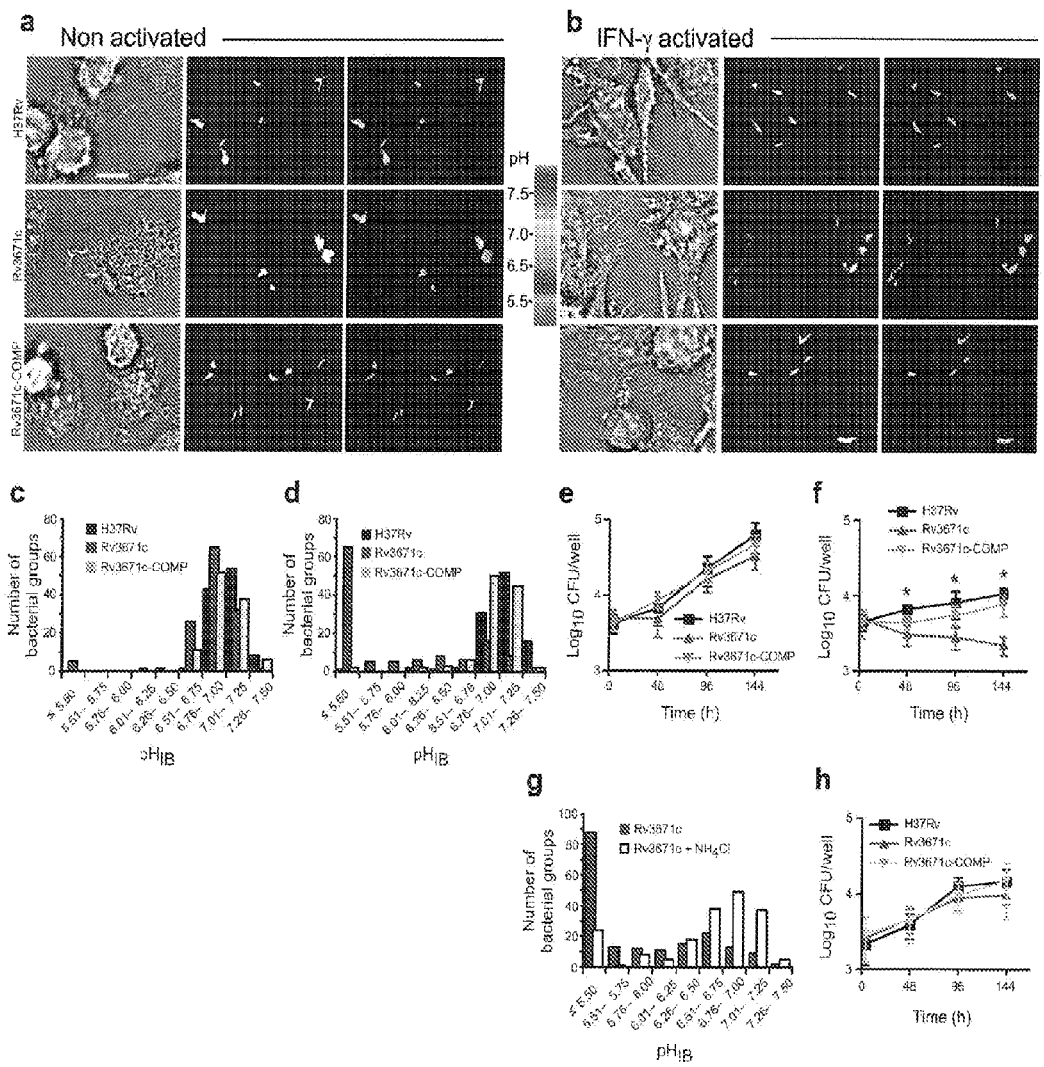
FIGS. 3A and 3B are transmitted images with overlays of bacteria in green (left), fluorescent bacteria (center) and pseudocolored images of the 410:470 excitation ratio (right) of nonactivated (FIG. 3A) and IFN-γ-activated (FIG. 3B) macrophages 24 h after infection with wild-type Mtb, the Rv3671c mutant, and the complemented mutant, each expressing pH-GFP. Scale bar, 10 μm.
FIGS. 3C and 3D are graphs showing the number of wild-type Mtb, Rv3671c mutant, and complemented mutant bacterial groups plotted against their $pH_{IB}$ in nonactivated (FIG. 3C) and IFN-γ activated (FIG. 3D) macrophages at 24 h after infection. There were 105-130 bacterial groups examined, and data represent three independent experiments.
FIGS. 3E and 3F graph CFU quantification of wild-type Mtb, the Rv3671c mutant, and the complemented mutant recovered from nonactivated (FIG. 3E) and IFN-γ-activated (FIG. 3F) macrophages at the indicated time points. Data are means±s.d. of two independent experiments, each in triplicate, and are representative of four independent experiments. *P<0.005 between wild-type and Rv3671c mutant bacteria, as determined by Student's two tailed t-test.
FIG. 3G shows the number of Rv3671c mutant bacterial groups plotted against their $pH_{IB}$ at 24 h after infection in IFN-γactivated macrophages left untreated or treated with 10 mM NH$_4$Cl. There were 185 bacterial groups examined, and data represent two independent experiments.
FIG. 3H illustrates quantification of CFU for wild-type Mtb, the Rv3671c mutant, and the complemented mutant recovered from IFN-γ-activated macrophages treated with 10 mM NH$_4$Cl. Data are means±s.d. of two independent experiments, each in triplicate.

Intrabacterial pH Measurements pH-GFP (Miesenböck et al., "Visualizing Secretion and Synaptic Transmission with pH-Sensitive Green Fluorescent Proteins," *Nature* 394:192-195 (1998), which is hereby incorporated by reference in its entirety) was cloned downstream of the mycobacterial promoter $P_{smyc}$ (Ehrt et al., "Controlling Gene Expression in *Mycobacteria* with Anhydrotetracycline and Tet Repressor," *Nucleic Acids Res* 33:e21 (2005), which is hereby incorporated by reference in its entirety) and Mtb strains were transformed with it. Early-log-phase cultures were adjusted to an $OD_{580}$ of 0.5 in 7H9-Tw medium, centrifuged at 3000 g and pellets were resuspended in an equal volume of pcit-Ty-7.4 or pcit-Ty-4.5 medium. All $pH_{IB}$ measurements were performed after incubation of bacteria at an $OD_{580}$ of 0.5 in the respective buffer. Triplicate 1-ml aliquots were incubated at 37° C. and concentrated fivefold by centrifugation to increase the GFP signal. Aliquots (100-µl) were analyzed in a Molecular Devices M5 plate reader, exciting at absorbances of 395 nm and 475 nm and recording emission at an absorbance of 510 nm. The $pH_{IB}$ was derived by interpolating the 395:475 absorbance ratios on a standard curve (FIG. 13A). For $pH_{IB}$ measurements of intraphagosomal bacteria, $1.5 \times 10^5$ bone marrow-derived mouse macrophages (BMDMs) were plated in glass-bottom No. 1.5 thickness poly-D-lysine-coated 35-mm culture dishes (MatTek). BMDMs were infected with Mtb at an multiplicity of infection of two for 2 h, then washed twice with PBS. For microscopy, BMDMs were placed in DMEM without phenol red (GibcoBRL) supplemented with 1% FBS, 0.58 g·l$^{-1}$ L-glutamine, 1 mM sodium pyruvate and 10 mM HEPES. A Leica DMIRB inverted fluorescence microscope fitted with a 63×1.4 numerical aperture objective and Chroma Technology pH-sensitive GFP filter set (exciters D410/30X and D470/20X, beamsplitter 500DCXR, emitter 535/50M) was used. Image acquisition and analysis was performed with a Photometrics CoolSnap HQ digital camera and MetaMorph v. 6.2r6 image analysis software (Universal Imaging). All images were acquired and analyzed within an experiment under identical conditions. For display in histograms, average bacterial group ratio intensities (FIGS. 3C, 3D, 3G and FIG. 8) were determined. A bacterial group was defined as at least one bacterium, but may consist of 2-5 bacilli. Pseudocolor images show pixel-by-pixel ratio intensities (FIGS. 3A-3B). All images at a given wavelength are shown at the same intensity settings or pseudocolor scale. The $pH_{IB}$ was derived by interpolating the 410:470 absorbance ratios on a standard curve (FIG. 13B).

Example 5

Immunoblotting

Lysates were prepared from mid-log-phase cultures in PBS containing protease inhibitor cocktail (Roche) by bead beating. Lysates were centrifuged at 18,000 g for 2 h at 4° C. to pellet cell walls. Supernatants were centrifuged at 100,000 g for 1 h at 4° C. to pellet cell membranes. Pellets were washed and resuspended in SDS sample buffer. For SDS-PAGE, 10 µg of cytosolic fractions and an equal volume of cell envelope fractions were loaded based on total volume of the fractions. Flag-specific (Sigma) and dihydrolipoamide S-acyltransferase-specific rabbit antisera were used.

Example 6

Complementation and Mutagenesis

Wild-type Rv3671c were cloned on an integrative vector conferring streptomycin resistance. The Rv3671c mutant was transformed by electroporation and selected transformants with 20 μg·ml$^{-1}$ streptomycin. A flag-tagged and S343A mutant Rv3671c were generated by PCR.

Example 7

Mycobacterium tuberculosis Survival in Macrophages

BMDMs were differentiated in DMEM (GibcoBRL) containing 20% L-cell medium, 10% FBS, 0.58 g·L$^{-1}$ L-glutamine, 1 mM sodium pyruvate, and 10 mM HEPES, providing a nearly pure macrophage population, as assessed by morphology and cell surface staining of the macrophage markers CD14, F4/80, Fc-γ receptor and major histocompatibility complex class II, the latter after IFN-γ activation. BMDMs were seeded with or without 10 ng·ml$^{-1}$ murine IFN-γ (R&D Systems). Sixteen hours later, macrophages were infected at a multiplicity of infection of 0.1 and then washed with PBS 4 h later. The medium was replaced every 48 h. BMDMs were lysed with 0.5% Triton X-100 and bacteria enumerated by plating serial dilutions of the lysate on 7H10 or 7H11 agar plates. Where indicated, 10 mM NH4Cl was added with IFN-γ before infection.

Example 8

Mouse Infections

C57BL/6 mice (Jackson Laboratories) were infected using an Inhalation Exposure System (Glas-Col) with early-log-phase Mtb to deliver ~100-200 bacilli per mouse or more where stated. Serial dilutions of organ homogenates from 4 or 5 mice per data point were plated on 7H10 or 7H11 agar plates to quantify CFU. The upper left lung lobes were fixed in 10% buffered formalin, embedded in paraffin and stained with H&E. Procedures involving mice were reviewed and approved by the Institutional Animal Care and Use Committee of Weill Cornell Medical College.

Example 9

Statistical Analyses

Statistical significance of the difference between experimental groups was determined by the two-tailed Student's t-test using PRISM Software. P values less than 0.05 were considered significant.

Example 10

Results and Discussion

Figure 5:
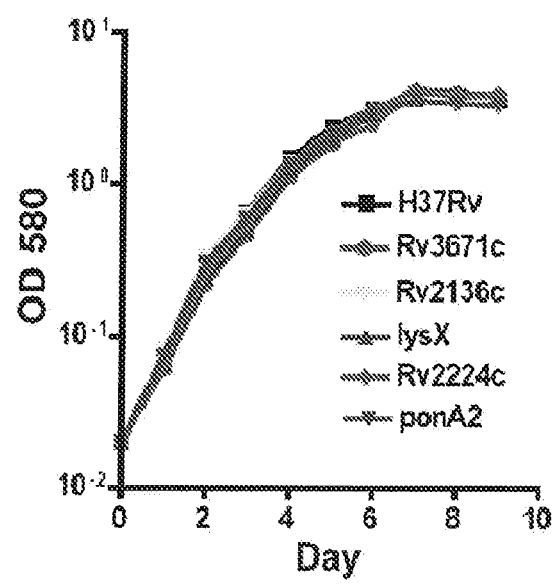
FIG. 5 is a graph showing acid-sensitive mutants display normal in vitro growth. Growth of wild-type Mtb (H37Rv) and mutants in 7H9-Tw at pH 6.6 was monitored by measuring the OD580 over a period of 9 days.
Figure 7:
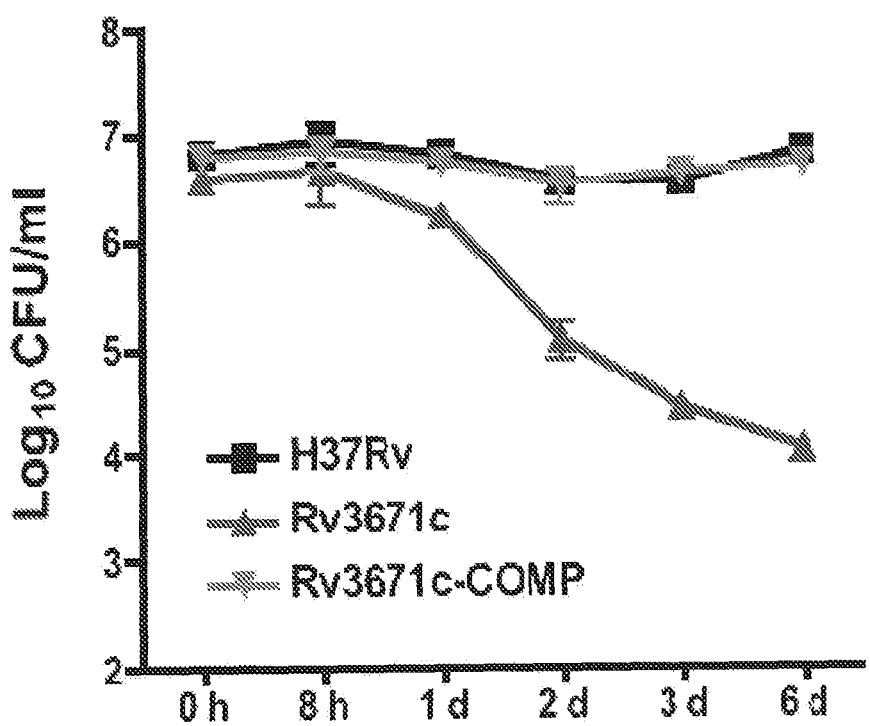
FIG. 7 is a graph showing the timecourse of survival of Mtb strains at pH 4.5. Wild-type Mtb (H37Rv, black line), Rv3671c mutant (red line) and complemented mutant (grey line) in pcit-Ty-4.5. h=hours, d=days.

Survival of Mtb was first monitored in standard 7H9 growth medium, which routinely contains Tween 80 as a dispersal agent so that colony-forming units (CFU) can be enumerated. When suspended in this medium at pH 6.6, Mtb grows logarithmically (FIG. 5). However, when the medium was acidified to pH 4.5 (7H9-Tw-4.5 medium), a culture containing 5×10$^6$ CFU ml$^{-1}$ Mtb was almost sterilized by day 15 (FIG. 1A). Mtb is highly susceptible to killing by free fatty acids (Dubos, R., "The Effect of Lipids and Serum Albumin on Bacterial Growth," *J. Exp Med* 85:9-22 (1947); Kanai et al., "Antibacterial and Cytotoxic Aspects of Long-Chain Fatty Acids as Cell Surface Events: Selected Topics," *Jpn J Med Sci Biol* 32:135-174 (1979); and Vandal et al., "Cytosolic Phospholipase A2 Enzymes are Not Required by Mouse Bone Marrow-Derived Macrophages for the Control of *Mycobacterium Tuberculosis* in Vitro," *Infect Immun.* 74:1751-1756 (2006), which are hereby incorporated by reference in their entirety), and it is possible that acid hydrolyzes Tween 80, releasing oleic acid. Alternatively, Tween 80's ability to strip the bacterium's glycoprotein capsule (Ortalo-Magne et al., "Identification of the Surface-Exposed Lipids on the Cell Envelopes of *Mycobacterium Tuberculosis* and Other Mycobacterial Species," *J Bacteriol* 178:456-461 (1996), which is hereby incorporated by reference in its entirety) might render Mtb sensitive to acid. To avoid Tween-associated artifacts, survival of Mtb was examined at pH 4.5 in 7H9 medium containing nonhydrolyzable Tyloxapol as the dispersing agent (7H9-Ty-4.5 medium). Killing in 7H9-Ty-4.5 medium was reduced, but not eliminated (FIG. 1B). Finally, in phosphate-citrate buffer at pH 4.5 containing Tyloxapol (pcit-Ty-4.5 buffer), 100% of Mtb survived (FIG. 1B). Thus, at least two components of the standard growth medium become toxic to Mtb at pH 4.5: one associated with Tween and another associated with albumin, and both may release free fatty acids at low pH.

Aside from the artifactual effects arising from the use of 7H9-Tw-4.5, wild-type Mtb was highly resistant to acid at pH 4.5, in that the bacteria were not killed in pcit-Ty-4.5 buffer. Therefore, the identification of genes responsible for the acid resistance and genes that conferred relative resistance to the combination of acid and 7H9-Tw medium was sought, because many experiments with Mtb are carried out in this medium. Of the 10,100 Mtb transposon mutants (Darwin et al., "The Proteasome of *Mycobacterium Tuberculosis* is Required for Resistance to Nitric Oxide," *Science* 302:1963-1966 (2003), which is hereby incorporated by reference in its entirety) that were screened individually for impaired ability to recover from a 6-d exposure to 7H9-Tw-4.5 medium, 34 mutants were identified containing transposons in 21 genes. Mutants with disruptions of the same gene carried independent transposon insertions at distinct sites (FIG. 14). Fifteen (71%) of the affected genes were annotated as involved in cell wall functions, such as peptidoglycan and lipoarabinomanan biosynthesis (e.g., pbpA, ponA2, glnA2, Rv2136c and ppm1) (Cole et al., "Deciphering the Biology of *Mycobacterium Tuberculosis* from the Complete Genome Sequence," *Nature* 393:537544 (1998), which is hereby incorporated by reference in its entirety). Mutants in only 5 of the 21 genes remained hypersensitive to pH 4.5 when Tween was replaced with Tyloxapol (FIG. 1C), and only two remained hypersensitive when 7H9 was replaced with pcit (FIG. 1D). None of the mutants showed a growth defect in 7H9-Tw medium at pH 6.6 (FIG. 5).

The two mutants that were acid sensitive in all three test media contained transposon insertions in Rv2136c and Rv3671c. Rv2136c encodes the Mtb homolog of *Escherichia coli* BacA, an undecaprenol phosphatase (El Ghachi et al., "The bacA Gene of *Escherichia Coli* Encodes an Undecaprenyl Pyrophosphate Phosphatase Activity," *J Biol Chem* 279: 30106-30113 (2004), which is hereby incorporated by reference in its entirety) involved in peptidoglycan assembly and resistance to bacitracin; the gene family contributes to in vivo survival in several bacterial species, including *Mycobacterium smegmatis* (Rose et al., "Involvement of *Mycobacterium Smegmatis* Undecaprenyl Phosphokinase in Biofilm and Smegma Formation," *Microbes Infect* 6:965-971 (2004), which is hereby incorporated by reference in its entirety). Rv3671c is predicted to be a serine protease with conserved aspartate, histidine and serine active site residues (FIG. 6) and four transmembrane domains (Cole et al., "Deciphering the Biology of *Mycobacterium Tuberculosis* from the Complete Genome Sequence," *Nature* 393:537544 (1998) and Rawlings et al., "MEROPS: the Peptidase Database," *Nucleic Acids Res* 34:D270-D272 (2006), which are hereby incorporated by reference in their entirety).

Figures 2A, 2B, 2C, 2D, 2E:
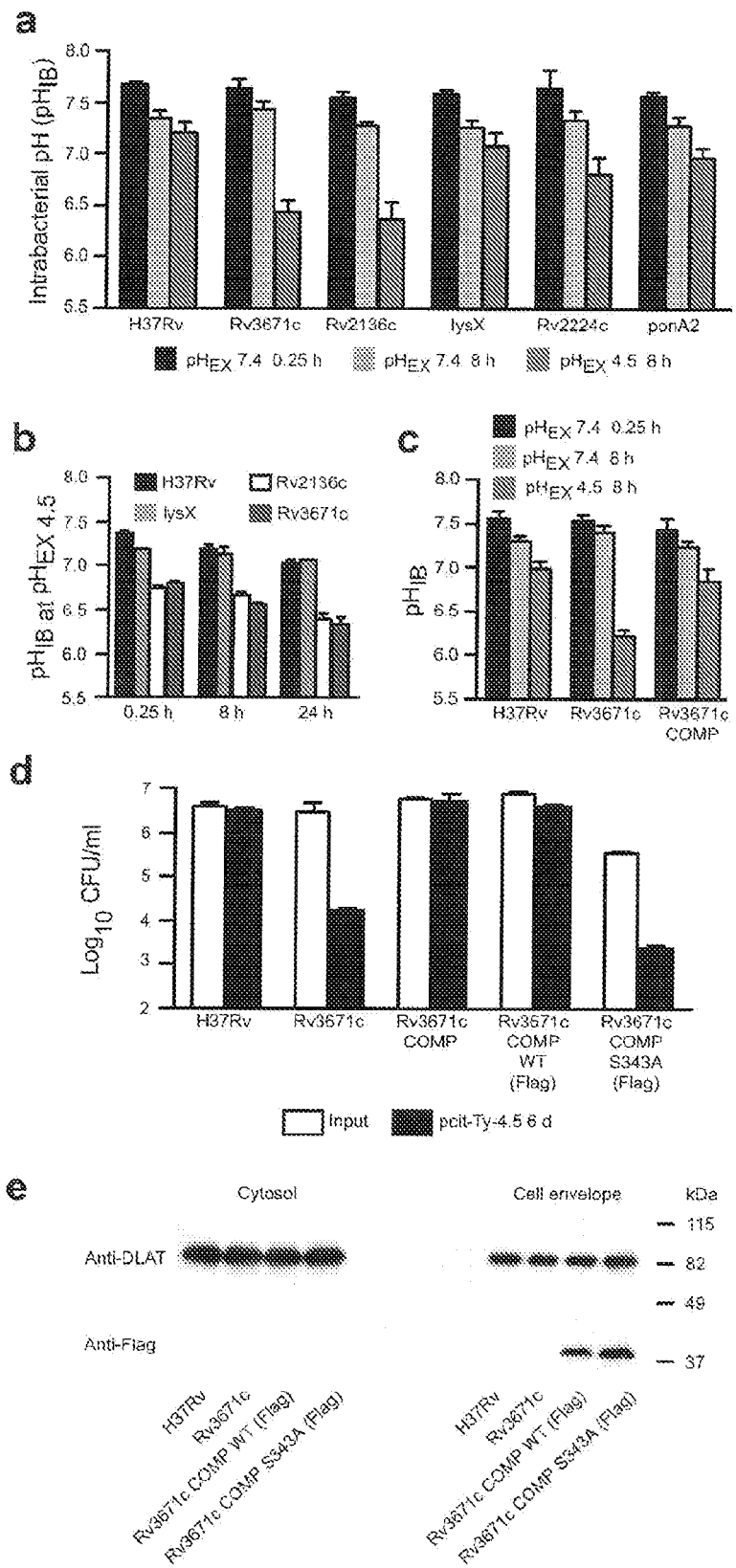
FIGS. 2A-2E show intrabacterial pH ($pH_{IB}$) measurements of acid-sensitive mutants and complementation of the Rv3671c mutant.

The intrabacterial pH ($pH_{IB}$) of wild-type and mutant Mtb strains was determined in near-neutral conditions, in acidified medium, and when the bacilli resided in macrophages that were either nonactivated or IFN-γ-activated. Each strain was transformed with a plasmid encoding a pH-sensitive ratiometric GFP (pH-GFP) (Miesenbock et al., "Visualizing Secretion and Synaptic Transmission with pH-Sensitive Green Fluorescent Proteins," *Nature* 394:192-195 (1998), which is hereby incorporated by reference in its entirety), which allowed for noninvasive measurements of $pH_{IB}$ on live cells. $pH_{IB}$ was monitored at intervals after transfer to pcit-Ty buffer. Basal $pH_{IB}$, calculated from measured ratio values, was 7.68±0.02 in wild-type Mtb, 7.65±0.08 in the Rv3671c mutant and 7.55±0.06 in the Rv2136c mutant (mean±s.d., n=3 experiments; FIG. 2A). After 8 hours in pcit-Ty-7.4 buffer, the $pH_{n3}$ fell slightly in all strains tested (FIG. 2A). In contrast, after an 8-hours incubation in pcit-Ty-4.5 buffer, the $pH_{IB}$ of wild-type Mtb dropped only to 7.20±0.11, whereas the $pH_{IB}$ of the Rv3671c and Rv2136c mutants fell to 6.44±0.11 and 6.37±0.15, respectively (FIG. 2A). Intrabacterial acidification preceded (FIG. 2B) and was associated with (FIG. 1D) a marked decline in viability. Therefore, the rapid influx of protons (<15 min) was the probable cause of death.

Because Rv2136c is part of a putative operon, and because the mutant phenotypes did not revert when the wild-type allele was provided in trans, further studies focused on the Rv3671c mutant. Transformation of the Rv3671c mutant with an integrative plasmid encoding a wild-type Rv3671c allele restored $pH_{is}$ homeostasis (FIG. 2C) and survival at pH 4.5 (FIG. 2D). Mutation of the Rv3671c active site serine (Ser343) to alanine abolished complementation of the Rv3671c mutant (FIG. 2D). Rv3671c protein was detected in equivalent amounts in the cell envelope fraction prepared from bacterial lysates of the complemented strains, both those with and those without the predicted active site serine (FIG. 2E). These data indicate that Rv3671c indeed encodes a membrane-associated protein whose function requires Ser343.

Figures 8A, 8B, 8C:
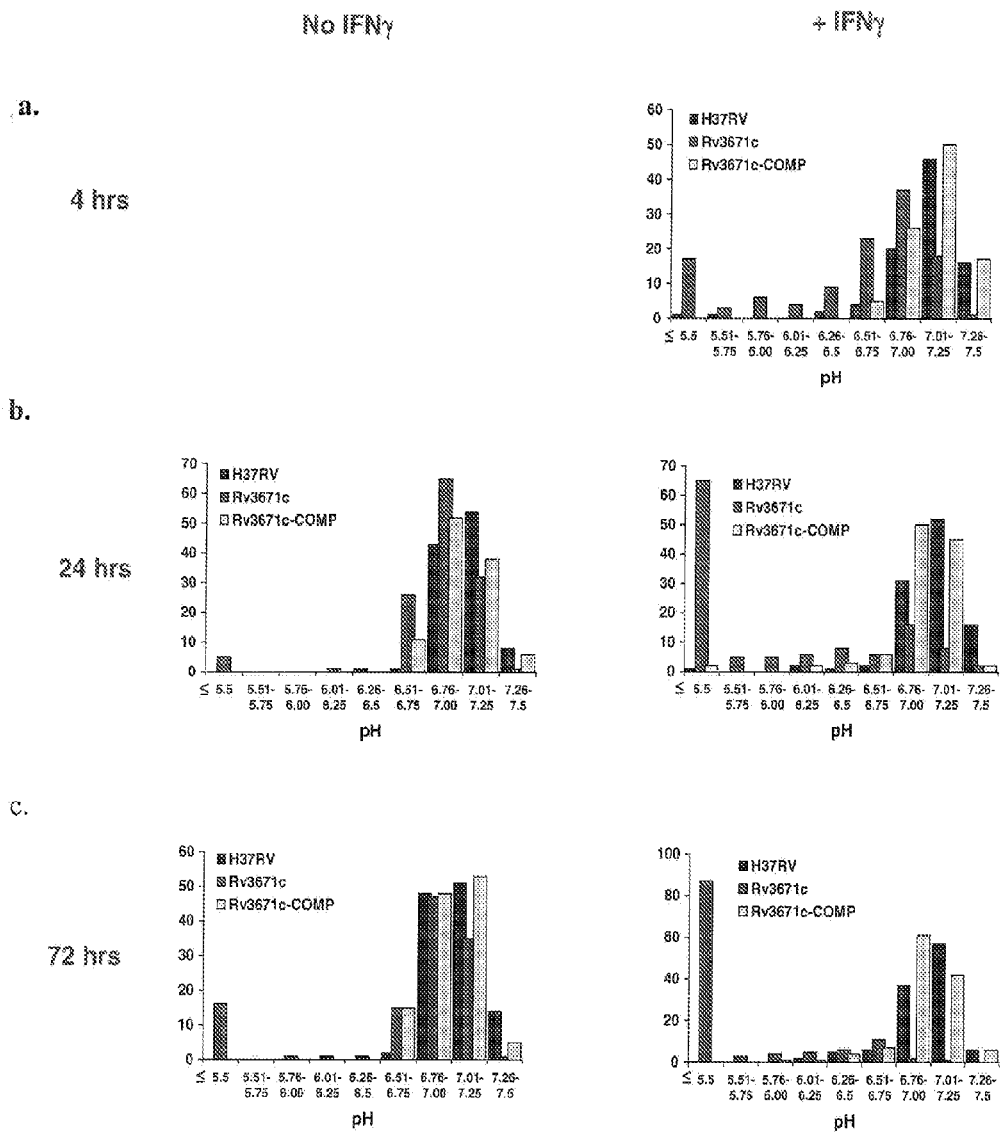
FIGS. 8A-C are graphs illustrating the kinetic analysis of $pH_{IB}$ in non-activated (left) and IFNγ-activated (right) macrophages. Number of wild-type Mtb (H37Rv, black bars), Rv3671c mutant (red bars), and complemented mutant (grey bars) bacterial groups plotted against their $pH_{IB}$ at 4 hours (FIG. 8A), 24 hours (FIG. 8B) and 72 hours (FIG. 8C) post infection. Macrophages were infected and visualized as described infra. The 24 hour time point is the same as shown in FIGS. 3C-3D.

Measurements of the $pH_{IB}$ of bacteria residing in macrophage phagosomes was then performed. Wild-type Mtb maintained its $pH_{IB}$ in both nonactivated and IFN-γ-activated macrophages at pH 6.76-7.50 (FIG. 3A-3D; "H37Rv"). In contrast, the Rv3671c mutant failed to control its $pH_{IB}$ in IFN-γ-activated macrophages, but was able to do so in nonactivated macrophages (FIGS. 3A-3D; "Rv3671c"). Most mutant bacteria had a $pH_{IB}$ of 5.5 or lower in phagosomes of IFN-γ-activated macrophages (FIG. 3D). Complementation of the Rv3671c mutant restored the defect in intraphagosomal $pH_{IB}$ maintenance (FIGS. 3A-3D; "Rv3671c-COMP"). Likewise, the Rv3671c mutant was killed by IFN-γ-activated (FIG. 3F) but not nonactivated macrophages (FIG. 3E). Kinetic analysis showed that the proportion of Rv3671c mutant bacteria that were acidified increased from 4 to 72 hours in IFN-γ-activated macrophages, whereas both wild-type Mtb and the complemented mutant maintained $pH_{IB}$ even at 72 h after infection (FIGS. 8A-8C). No defect in the $pH_{IB}$ of the strains in nonactivated macrophages were observed at 72 hours after infection (FIG. 8C). The ability of the Rv3671c mutant to maintain $pH_{IB}$ in nonactivated macrophages indicates that it remains capable of restricting phagosome acidification. As observed for the Rv3671c mutant in vitro, in IFN-γ-activated macrophages, intrabacterial acidification preceded a decline in viability of the bacteria and is probably the primary cause of death of the mutant. Accordingly, treatment of IFN-γ-activated macrophages with the alkalinizing weak base $NH_4Cl$ (Hart et al., "Ammonium Chloride, an Inhibitor of Phagosome-Lysosome Fusion in Macrophages, Concurrently Induces Phagosome-Endosome Fusion, and Opens a Novel Pathway Studies of a Pathogenic *Mycobacterium* and a Nonpathogenic Yeast," *J Exp Med* 174: 881-889 (1991), which is hereby incorporated by reference in its entirety), which prevents acidification of phagosomes, protected $pH_{IB}$ of the mutant (FIG. 3G) and restored its survival (FIG. 3H).

Figures 4A, 4B, 4C, 4D:
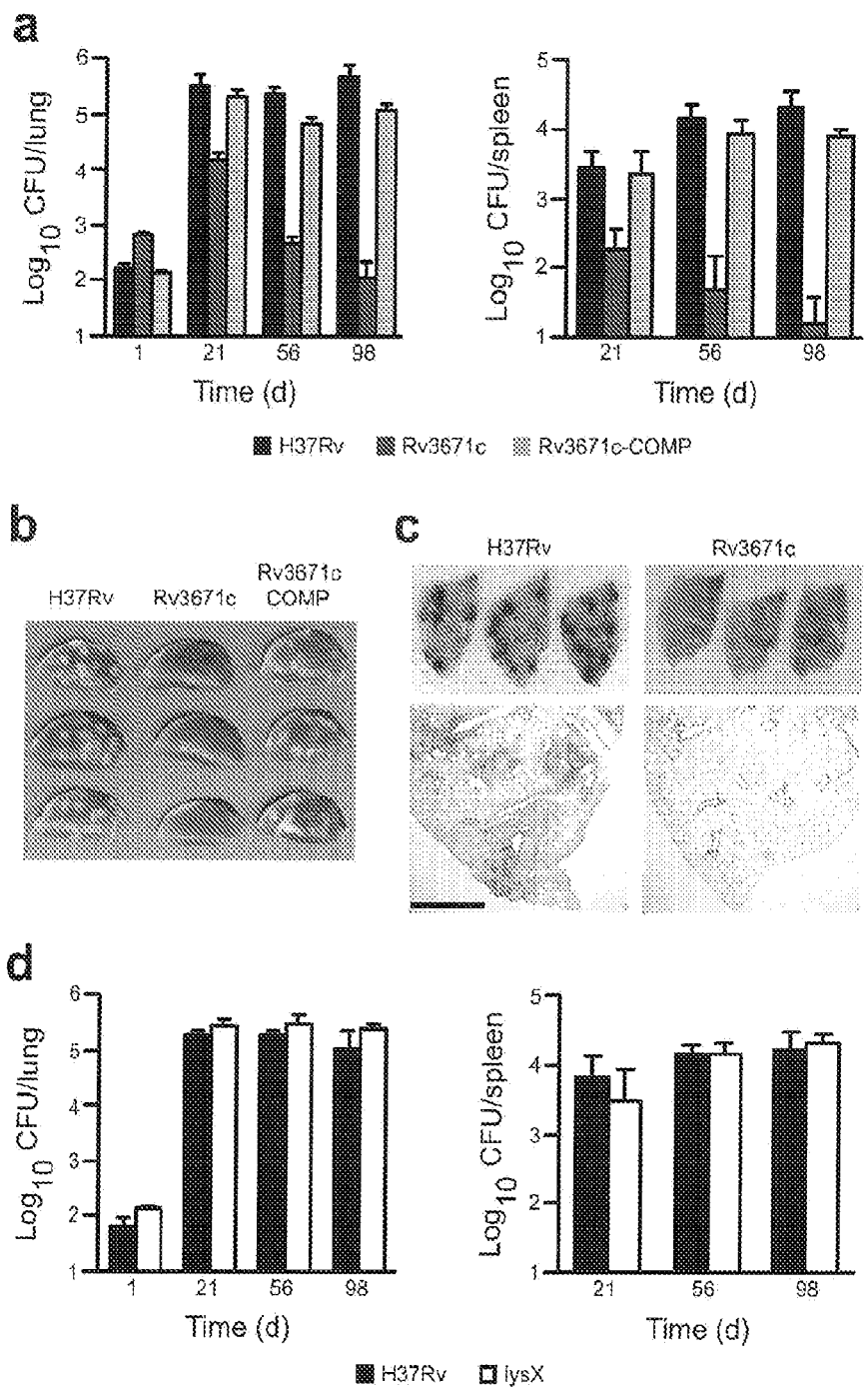
FIGS. 4A-D illustrate the requirement of Rv3671c for Mtb growth and persistence in vivo. The graphs of FIG. 4A show lung (left graph) and spleen (right graph) bacterial loads from mice infected with wild-type Mtb, the Rv3671c mutant, or the complemented mutant at the indicated time points. At days 56 and 98, the CFU from two and three out of five Rv3671c mutant infected mice, respectively, were below the limit of detection in the spleen. Data are means±s.d. from five mice per time point per group and represent three independent experiments; the limit of detection was 10 CFU per lung. The gross pathology of lungs infected with wild-type Mtb, the Rv3671c mutant, and the complemented mutant at day 56 are shown in FIG. 4B. The length of each lung lobe is 1.2 cm. Lung sections stained with H&E from mice infected with wild-type Mtb and Rv3671c mutant bacteria at day 56 are shown in FIG. 4C. Top images show unmagnified sections. The length of each lung lobe is 1.2 cm. Scale bar 1.0 mm for bottom images. The graphs of FIG. 4D show lung (left graph) and spleen (right graph) bacterial loads from mice infected with wild-type Mtb and the lysX mutant at the indicated time points. Data are means±s.d. from four mice per time point per group and represent two independent experiments.

The Rv3671c mutant was severely impaired for growth in mice infected by inhalation (FIG. 4A). At 21 d after infection, titers of the Rv3671c mutant in lungs and spleens were more than 1.0 log lower than for wild-type Mtb (FIG. 4A), despite a 0.6-log higher inoculum. In C57BL/6 mice, a robust adaptive immune response is initiated within about 21 days after inhalation of low numbers of Mtb, at which point IFN-γ is produced, bacterial growth is restricted and Mtb persists at a near-constant titer for about a year (North et al., "Immunity to Tuberculosis," *Annu Rev Immunol* 22:599-623 (2004), which is hereby incorporated by reference in its entirety). In contrast, when mice were infected with the Rv3671c mutant, the mutant was killed progressively in the lung and spleen after day 21, such that at least 3.6-log and 3.0-log fewer mutant bacteria were recovered from lungs and spleens, respectively, at day 98 as compared to wild-type bacteria (FIG. 4A). This indicates that Rv3671c is required not only for exponential growth of Mtb but also for its persistence in the face of an activated immune system. The Rv3671c mutant induced markedly less pulmonary pathology than wild-type bacteria (FIGS. 4B-4C). Complementation restored full virulence indicating that attenuation of the Rv3671c mutant in mice was solely due to the disruption of Rv3671c (FIGS. 4A-4B)

Figures 9A, 9B:
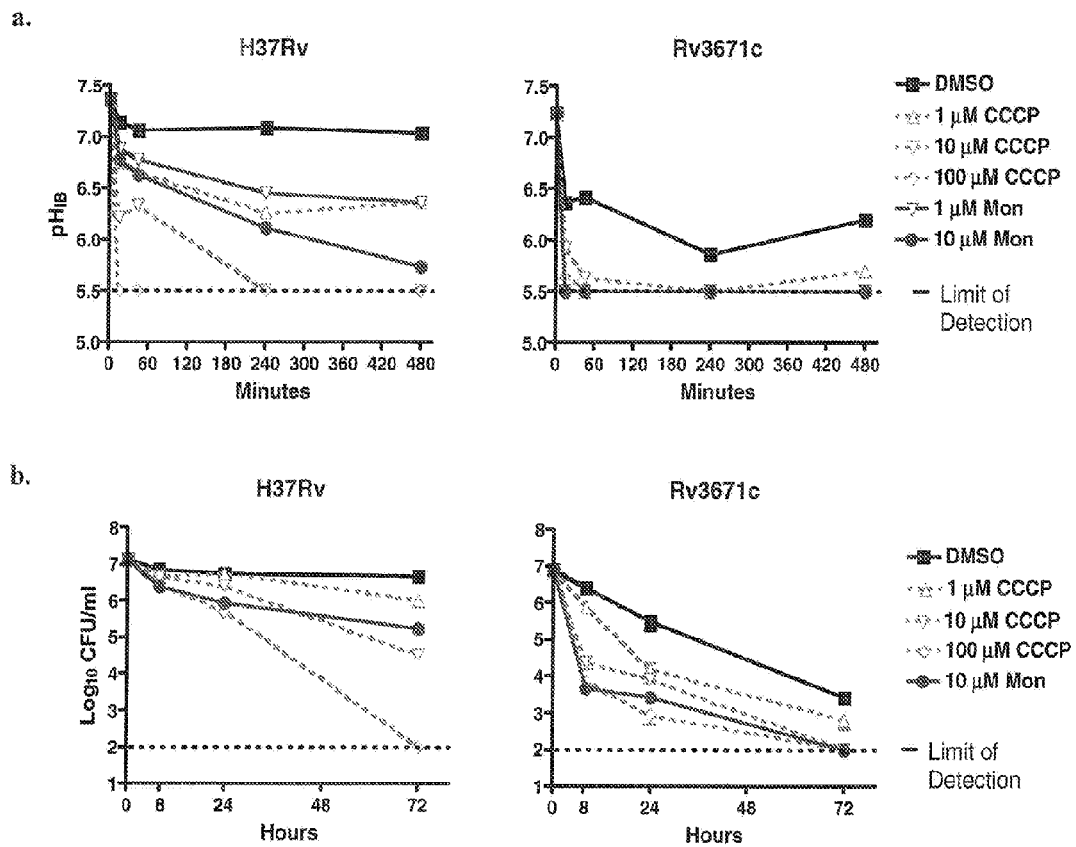
FIGS. 9A-9B are graphs showing the impact of carbonyl cyanide m-chlorophenylhydrazone (CCCP) and monensin on intrabacterial pH ($pH_{IB}$) and survival of wild-type Mtb (H37Rv) and the Rv3671c mutant. $pH_{IB}$ measurements of wild-type Mtb (H37Rv) and the Rv3671c mutant after treatment of the bacteria with the vehicle control DMSO, the protonophore CCCP or ionophore monensin in pcit-Ty-4.5 are shown in FIG. 9A. The 0-minute measurement is the $pH_{IB}$ of the strains in pcit-Ty-7.4. The limit of detection is pH 5.5. Data are means of duplicate measurements and represent two independent experiments.
Figures 10A, 10B:
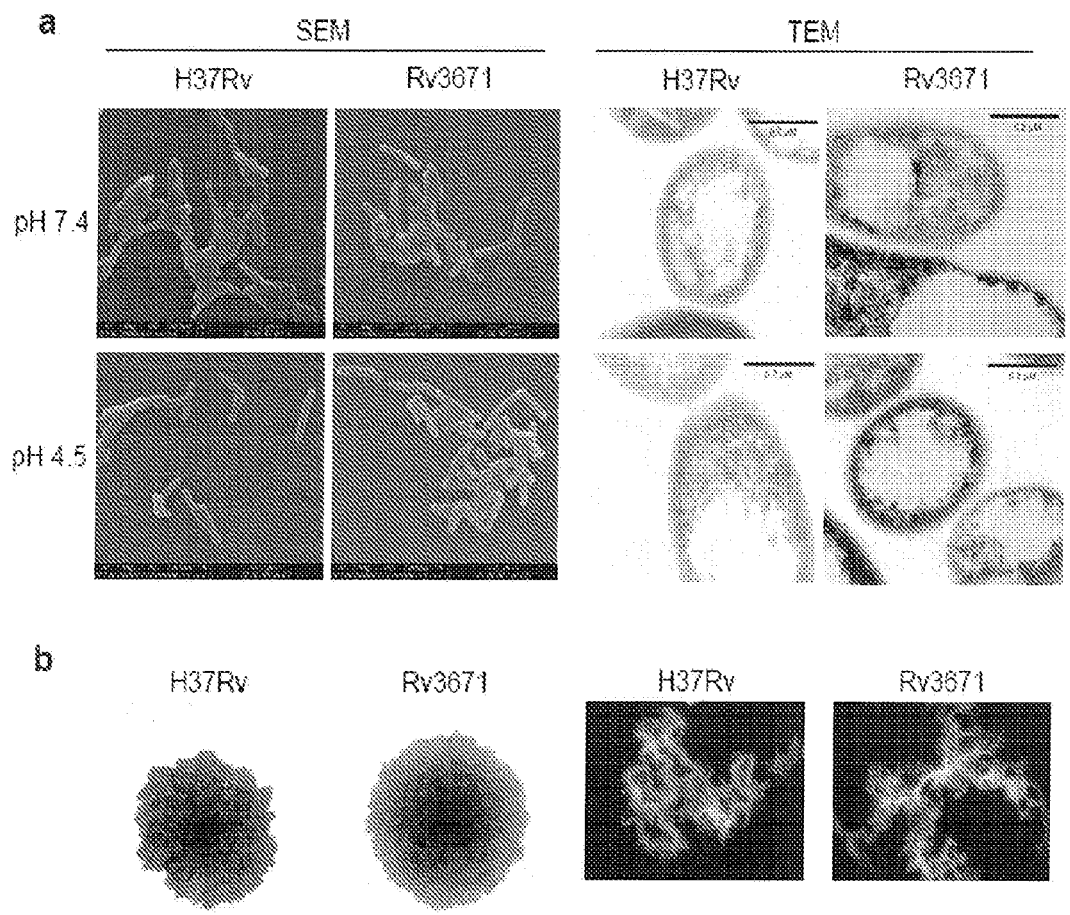
FIGS. 10A-10B show a morphological analysis of the Rv3671c mutant. Mtb strains were exposed to phosphate-citrate buffer at pH 7.4 or pH 4.5 for 24 hours and then processed for transmission electron microscopy (TEM) (FIG. 10A; right) and scanning electron microscopy (SEM) (FIG. 10A; left). The presumptive peptidoglycan layer exhibits a bilayered structure as has been described for Mtb (Takade et al., "Comparative Studies of the Cell Structures of *Mycobacterium Leprae* and *M. Tuberculosis* Using the Electron Microscopy Freeze-Substitution Technique," *Microbiol Immunol* 47:265-70 (2003), which is hereby incorporated by reference in its entirety).
Figures 11, 12:
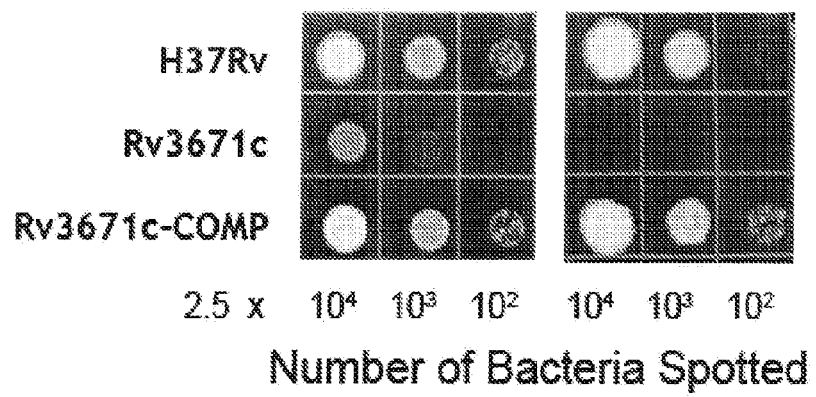
FIG. 11 is a table showing the sensitivity of Rv3671c and lysX mutants to antibiotics. Wild-type Mtb (H37Rv) and mutants were grown to early log phase and diluted to an ($OD_{580}$ of 0.01 in 7H9-Tw. Bacteria were then exposed to 2-fold dilutions of the indicated reagents. The minimum inhibitory concentration (MIC) was recorded as the minimum concentration at which no growth was observed after 2-3 weeks. Erythromycin (Erythr), rifampin, chloramphenicol (chloramp) represent the lipophilic antibiotics, indicated by shading in grey; and ethambutol (etham), isoniazid (INH), streptomycin (strep) are non-lipophilic antibiotics. MIC values for the antibiotics are in µg/ml. The antibiotic MIC assays are representative of 3 independent experiments. The erp mutant is included as a positive control because the Mtb and *Mycobacterium smegmatis* erp mutants have cell wall defects and the *Mycobacterium marinum* erp mutant is hypersensitive to the lipophilic antibiotics (Berthet et al., "Attenuation of Virulence by Disruption of the *Mycobacterium Tuberculosis* Erp Gene," *Science* 282:759-62 (1998); Cosma et al., "*Mycobacterium Marinum* Erp is a Virulence Determinant Required for Cell Wall Integrity and Intracellular Survival," *Infect Immun* 74:3125-33 (2006) and Kocincova et al., "The Erp Protein is Anchored at the Surface by a Carboxy-Terminal Hydrophobic Domain and is Important for Cell-Wall Structure in *Mycobacterium Smegmatis*," *FEMS Microbiol Lett* 231:191-6 (2004), which are hereby incorporated by reference in their entirety).
FIG. 12 depicts the sensitivity of the Rv3671c mutant to SDS. For exposure to SDS, Mtb strains were grown to early log phase and diluted to an $OD_{580}$ of 0.01 in 7H9-Tw. A 10-fold dilution series was made from 0.01 to 0.0001 $OD_{580}$ in 7H9-Tw and 5 µl were spotted on 7H10 agar plates containing 10% OADC with or without 0.01% SDS. Growth was visualized 10-14 days later. Data is representative of 3 independent experiments.
Figure 15:
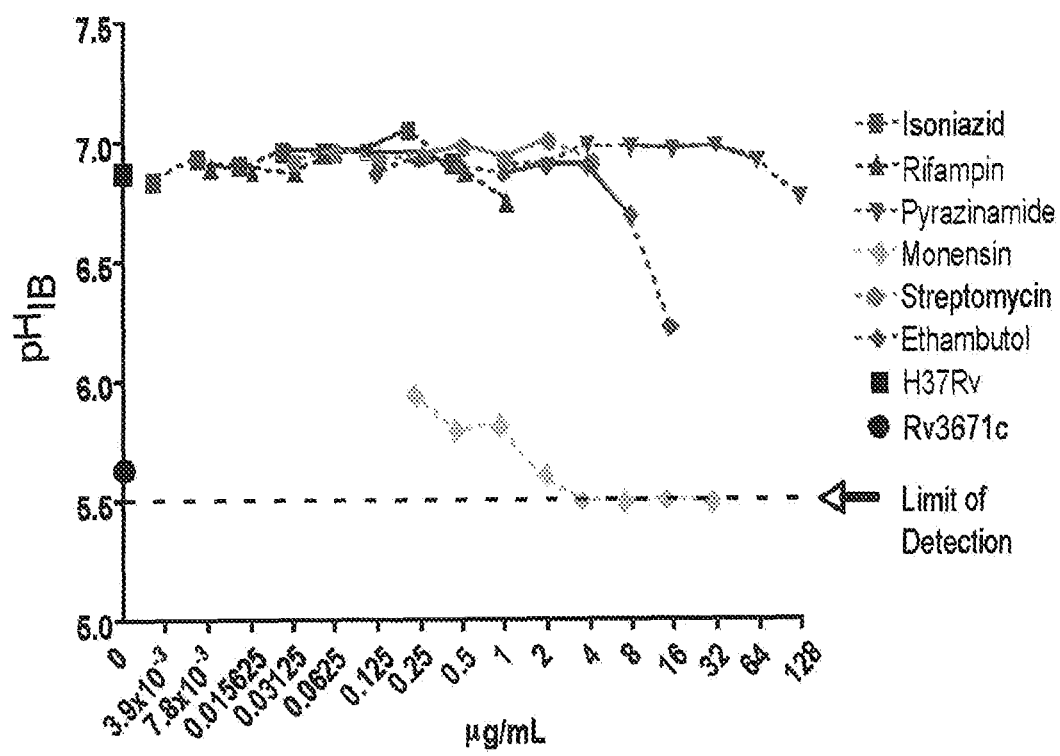
FIG. 15 is a graph illustrating the effects of antibiotics, monensin and natural product compounds on $pH_{IB}$ of Mtb. Wild-type H37Rv transformed with pH-GFP was treated with vehicle control DMSO, antibiotic, or monensin in phosphate citrate buffer pH 4.5. As a positive control, Rv3671c::tn was exposed to phosphate citrate buffer pH 4.5. 395/475 ratio measurements were obtained after 24 hours of exposure and converted to $pH_{IB}$ with reference to a standard curve. Solid segments of lines represent reported MIC ranges for each of the antibiotics tested.
Figure 16:
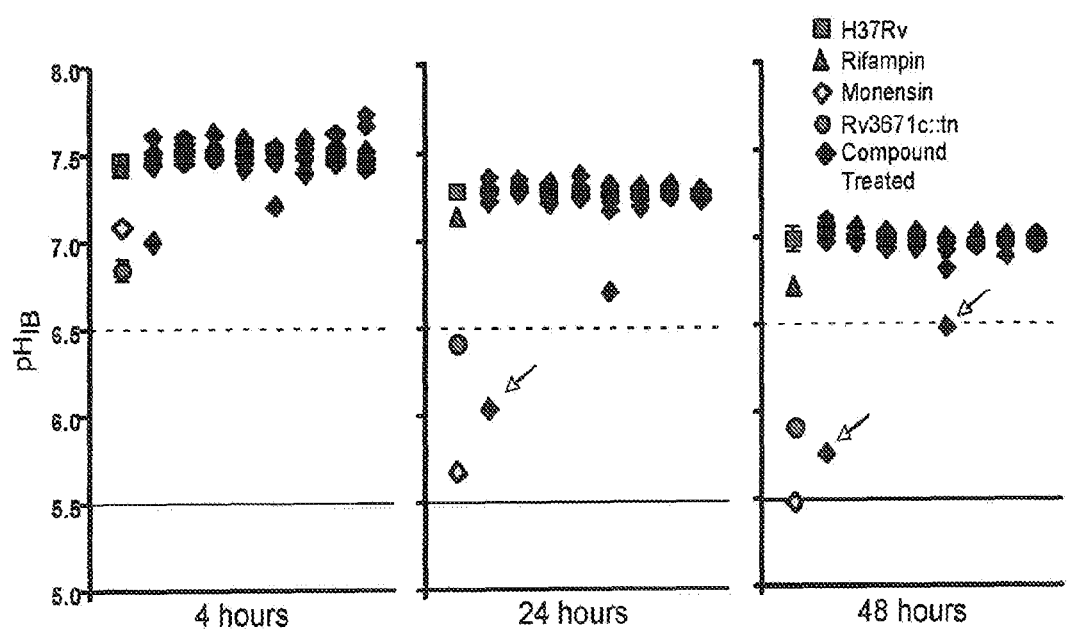
FIG. 16 shows results of a high-throughput screen of potential inhibitors of pH homeostasis in Mtb. H37Rv transformed with pH-GFP was treated with vehicle control DMSO (red square), rifampin (blue triangle), monensin (yellow diamond) or natural products (black diamonds) at 12.5 µM in phosphate citrate buffer pH 4.5. Rv3671c::tn was included as positive control. 395/475 ratio measurements were obtained after 4, 24, and 48 hours of exposure and converted to pHIB with reference to a standard curve. The dashed line indicates the cut-off and the solid line indicates the limit of detection. Data from one 96-well plate are shown. Two candidate hits are marked with arrows.

Rv3671c is a membrane protein but does not contain a PDZ protein-protein interaction domain, and as such is distinct from bacterial periplasmic HtrA (high temperature requirement A) proteins, of which Mtb is predicted to have at least three (Cole et al., "Deciphering the Biology of *Mycobacterium Tuberculosis* from the Complete Genome Sequence," *Nature* 393:537544 (1998) and Mohamedmohaideen et al., "Structure and Function of the Virulence-Associated High-Temperature Requirement A of *Mycobacterium Tuberculosis*," *Biochemistry* 47:6092-6102 (2008), which are hereby incorporated by reference in their entirety). It may protect Mtb from acid by modifying the bacterial cell envelope, regulating protein or lipid quality control and/or serving in signaling pathways that help the bacterium resist extracellular stresses. Expression of Rv3671c mRNA was constitutive and not induced after exposure of Mtb to low pH in vitro or in nonactivated and IFN-γ-activated macrophages (Rohde et al., "*Mycobacterium Tuberculosis* Invasion of Macrophages: Linking Bacterial Gene Expression to Environmental Cues," *Cell Host Microbe* 2:352-364 (2007), which is hereby incorporated by reference in its entirety). Treatment of the Rv3671c mutant with the protonophore carbonyl cyanide m-chlorophenylhydrazone or the ionophore monensin further reduced the mutant's $pH_{IB}$ (FIG. 9A) and further attenuated its survival in pcit-Ty-4.5 medium (FIG. 9B), indicating that Rv3671c-independent mechanisms of $pH_{IB}$ homeostasis exist. Despite its susceptibility to extracellular protons, the Rv3671c mutant's cell wall was not grossly altered, as the mutant bacterium resembled the wild-type Mtb in its colony morphology (FIG. 10B; left), formation of cords (FIG. 10B; right) and cell structure (FIG. 10A) as visualized by transmission and scanning electron microscopy at both neutral and acidic pHs. However, the Rv3671c mutant was hypersensitive to the cell wall-damaging detergent SDS and to the lipophilic antibiotics erythromycin and rifampin, suggesting that it has some defect in cell wall function (FIGS. 11 and 12). A mutant containing a transposon in lysX, which is annotated to encode a lysyl-tRNA synthetase, was also hypersensitive to erythromycin and rifampin (FIG. 11) and as susceptible as the Rv3671c mutant to acid in 7H9-Tw-4.5 and 7H9-Ty-4.5 media (FIG. 1C). However, the mutant was capable of maintaining $pH_{IB}$ and was as viable as wild-type Mtb in pcit-Ty-4.5 medium (FIGS. 2A and 1D). The lysX mutant was also fully virulent in mouse lungs and spleens (FIG. 4D). Thus, a defect in $pH_{IB}$ maintenance was associated with severe attenuation in vivo.

Mtb survives within macrophages by preventing fusion of phagosomes with lysosomes, but it also persists within acidic phagolysosomes in activated macrophages. Ratiometric fluorescence measurements were used on live bacteria to show that Mtb is acid resistant and is able to control its $pH_{IB}$ in acidic conditions in vitro and within both nonactivated and activated macrophages. In the absence of Rv3671c, Mtb was unable to maintain $pH_{IB}$ and survive within activated macrophages. As acid promotes the activity of numerous host defenses, such as lysosomal hydrolases and reactive oxygen and nitrogen intermediates, the marked attenuation of the Rv3671c mutant in vivo is probably due to the synergistic interaction of phagosomal acid with other macrophage products. For instance, nitric oxide, whose accumulating autooxidation product nitrite ($NO_2$) can (re)generate the radicals NO and $NO_2$ at low pH (Stuehr et al., "A Macrophage Product Responsible for Cytostasis and Respiratory Inhibition in Tumor Target Cells," *J Exp Med* 169:1543-1555 (1989), which is hereby incorporated by reference in its entirety), is likely to become more potent within the acidified bacterial cytosol of the Rv3671c mutant. The vulnerability of the mutant to the host environment recommends the Rv3671c protein as a suitable drug target, notwithstanding that the mutant's normal growth in vitro under standard conditions would exclude the protein's candidacy by conventional criteria (Nathan C., "Antibiotics at the Crossroads," *Nature* 431: 899-902 (2004), which is hereby incorporated by reference in its entirety). Identification of molecular pathways used by intracellular pathogens for $pH_{IB}$ homeostasis in acidic compartments of host cells is likely to reveal new targets for chemotherapy.

Example 11

Development of a pH-GFP Based Screen to Identify Small Inhibitors of pH Homeostasis in Mtb The ratiometric pH-GFP provides a non-invasive means for measuring intrabacterial pH values between 5.5 and 8.5 as shown in calibration curve of pH-GFP of FIG. 9. The affect of different antibiotics and the ionophore monensin on Mtb's $pH_{IB}$ in phosphate citrate buffer at pH 4.5 were measured (FIG. 15). As expected, the ionophore monensin caused a concentration dependent decline in $pH_{IB}$. In contrast, isoniazid, rifampin, pyrazinmide and streptomycin did not significantly alter $pH_{IB}$ even at concentrations that were above the minimal inhibitory concentration (MIC) of the antibiotics. Ethambutol caused a substantial decline in $pH_{IB}$ at concentrations of ≥8 μg/ml. Based on these findings a trial screen was performed using the 395/475 fluorescence ratios of Mtb::pH-GFP as readout, with monensin and Rv3671c:tn as positive controls and rifampin as a negative control. The compounds screened were 1980 Analyticon purified, structurally identified natural products of microbial and plant origin.

Twenty-four candidate hits that caused a decline in Mtb's $pH_{IB}$ to 6.5 or lower were identified (FIG. 16). The Z-factor values for all 25 plates screened using negative (H37Rv DMSO-treated) and positive (Rv3671c::tn) control wells were 0.76±1.2 for 4 hour, 0.86±0.07 for 24 hour and 0.89±0.05 for 48 hour measurements indicating high quality and power of this assay. The identification of small molecules inhibitors of Mtb pH homeostasis is thus feasible.

For high-throughput screening, candidate compound inhibitors of pH homeostasis in Mtb in dimethylsulfoxide (DMSO) are robotically dispensed to black-walled, clear-bottom 96-well plates containing 50 μL of phosphate citrate buffer with tyloxapol at pH 4.5 such that the final concentrations are test agent 12.5 μM, DMSO 0.25% and tyloxapol 0.02%. Wild-type Mtb H37Rv transformed with ratiometric GFP and the similarly transformed MtbΔRv3671c are used for the screen. Both strains are grown to mid log phase in 7H9 broth, washed twice, resuspended in phosphate citrate buffer with tyloxapol at pH 4.5 to a concentration of $OD_{580}$ nm=0.14 and dispensed in 0.150 ml per well with multi-channel pipettes to a final $OD_{580}$ nm=0.1. The negative control is wild-type Mtb exposed to vehicle (DMSO) alone. The positive controls are a conditional Rv3671c mutant (MtbΔRv3671c) and wild-type Mtb exposed to 10 μM monensin. Positive and negative controls are included on each plate in triplicate. At 4, 24, and 48 hours, the fluorescence of each well is read on a tunable Molecular Devices spectrofluorometer at excitation 395 nm, emission 510 nm and at excitation 475 nm, emission 510 nm. The ratio of both readings is recorded for each well and converted to $pH_{IB}$ with reference to a standard curve.

Z-values are calculated for each plate from the positive and negative controls. If a plate has Z<0.5, its results will be discarded and the screen repeated. For technically acceptable plates, results for each well are plotted for $pH_{IB}$ at each time point. Potential hits will be scored as any compound for which the $pH_{IB}$ of wild-type Mtb is <pH 6.5 because this internal pH is associated with a 1 log 10 drop in CFU when MtbΔRv3671c is incubated in buffers of various pH. Potential hits are compared to each other for chemical similarity via the Collaborative Drug Discovery (Burlingame, Calif.) server by Tanimoto indices.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of inhibiting growth of *Mycobacterium* comprising:

exposing *Mycobacterium* to an agent selected from the group consisting of 6-(3-butyryl-2,6-dihydroxy-4-methoxy-5-methylbenzyl)-3,5-dihydroxy-4,6-dimethyl-2-(2-methylbutanoyl)cyclohexa-2,4-dienone; (Z)-2-(3-hydroxy-5-oxo-4-pentylfuran-2(5H)-ylidene) acetic acid; 4-(2-methylbutanoyloxy)-5-(octanoyloxy)-2-((3,4,5-trihydroxy-6-(hydroxymethyl)tetrahydro-2H-pyran-2-yloxy)methyl)-6-(2,3,5-trihydroxy-6-(hydroxymethyl)tetrahydro-2H-pyran-4-yloxy) tetrahydro2H-pyran-3-yl decanoate; 2-hydroxy-4-methoxy-3-(3-methylbut-2-enyl)-6-pentylbenzoic acid; and 2-hydroxy-3-(2-hydroxy-3-methylbut-3-enyl)-4-methoxy-6-phenethylbenzoic acid under conditions effective to disrupt intrabacterial pH homeostasis and inhibit growth of the *Mycobacterium*.

2. The method according to claim 1, wherein said exposing is carried out under pH conditions that are different than that of the intrabacterial pH homeostatic conditions.

3. The method according to claim 2, wherein said exposing is carried out under acidic pH conditions.

4. The method according to claim 1, wherein the *Mycobacterium* is selected from the group consisting of *Mycobacterium tuberculosis*, *Mycobacterium avium-intracellulare*, *Mycobacterium kansasii*, *Mycobacterium bovis*, *Mycobacterium bovis* BCG, *Mycobacterium africanum*, *Mycobacterium canetti*, *Mycobacterium caprae*, *Mycobacterium pinnipedii*, *Mycobacterium ulcerans*, and *Mycobacterium leprae*.

5. The method according to claim 4, wherein the *Mycobacterium* is *Mycobacterium tuberculosis*.

6. A method of treating a bacterial *Mycobacterium* infection in a subject comprising
administering to the subject an agent selected from the group consisting of 6-(3-butyryl-2,6-dihydroxy-4methoxy-5-methylbenzyl)-3,5-dihydroxy-4,6-dimethyl-2-(2-methylbutanoyl)cyclohexa-2,4-dienone; (Z)-2-(3-hydroxy-5-oxo-4-pentylfuran-2(5H)-ylidene)acetic acid; 4-(2-methylbutanoyloxy)-5-(octanoyloxy)-2-((3,4,5-trihydroxy-6-(hydroxymethyl) tetrahydro-2H-pyran-2-yloxy)methyl)-6-(2,3,5-trihydroxy-6-(hydroxymethyl)tetrahydro-2H-pyran-4-yloxy) tetrahydro2H-pyran-3-yl decanoate; 2-hydroxy-4-methoxy-3-(3-methylbut-2-enyl)-6-pentylbenzoic acid; and 2-hydroxy-3-(2-hydroxy-3-methylbut-3-enyl)-4-methoxy-6-phenethylbenzoic acid under conditions effective to disrupt intrabacterial pH homeostasis and treat the *Mycobacterium* infection.

7. The method according to claim 6 further comprising selecting a subject having a *Mycobacterium* infection prior to said administering.

8. The method according to claim 6, wherein the *Mycobacterium* is selected from the group consisting of *Mycobacterium tuberculosis*, *Mycobacterium avium-intracellulare*, *Mycobacterium kansasii*, *Mycobacterium bovis*, *Mycobacterium bovis* BCG, *Mycobacterium africanum*, *Mycobacterium canetti*, *Mycobacterium caprae*, *Mycobacterium pinnipedii*, *Mycobacterium ulcerans*, and *Mycobacterium leprae*.

9. The method according to claim 8, wherein the *Mycobacterium* is *Mycobacterium tuberculosis*.

10. The method according to claim 6, wherein the agent is administered in combination with one or more antibacterial agents.

11. The method according to claim 10, wherein the one or more antibacterial agents are selected from the group consisting of isoniazid, rifampin, rifabutin, rifapentine, pyrazinamide, and ethambutol.

* * * * *